(12) United States Patent
Michielli et al.

(10) Patent No.: US 8,870,921 B2
(45) Date of Patent: Oct. 28, 2014

(54) SPINAL CROSS CONNECTORS

(71) Applicant: DePuy Synthes Products, LLC, Raynham, MA (US)

(72) Inventors: Michael Michielli, Medway, MA (US);
Philip A. Cormier, Quincy, MA (US);
Ernest Quintanilha, Norton, MA (US);
Joseph T. Stalaboin, Coventry, RI (US);
Holly R. Brideau, West Roxbury, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/723,982

(22) Filed: Dec. 21, 2012

(65) Prior Publication Data

US 2013/0116731 A1    May 9, 2013

Related U.S. Application Data

(63) Continuation of application No. 11/557,699, filed on Nov. 8, 2006, now Pat. No. 8,361,117.

(51) Int. Cl.
*A61B 17/70* (2006.01)

(52) U.S. Cl.
CPC ......... *A61B 17/7049* (2013.01); *A61B 17/7052* (2013.01)
USPC ........... 606/250; 606/252; 606/253; 606/251; 606/278

(58) Field of Classification Search
USPC .......................... 606/250–253, 272, 276–278
See application file for complete search history.

(56) References Cited

U.S. PATENT DOCUMENTS

| 180,881 A | 8/1876 | Howson |
|---|---|---|
| 457,964 A | 8/1891 | Bolte |
| 483,342 A | 9/1892 | Bolte |
| 596,729 A | 1/1898 | White |
| 900,717 A | 10/1908 | Feaster |
| 1,455,441 A | 5/1923 | Hodny |
| 2,638,301 A | 5/1953 | Smith |
| 3,012,091 A | 12/1961 | Schiffmann |
| 3,019,504 A | 2/1962 | Castagliuolo |

(Continued)

FOREIGN PATENT DOCUMENTS

| DE | 867422 C | 2/1953 |
|---|---|---|
| DE | 3219575 A1 | 12/1983 |

(Continued)

OTHER PUBLICATIONS

Asher, et al., "A Modular Spinal Rod Linkage System to Provide Rotational Stability", Spine, vol. 13, No. 3, pp. 272-277, 1998.

(Continued)

*Primary Examiner* — Eduardo C Robert
*Assistant Examiner* — Julianna N Harvey
(74) *Attorney, Agent, or Firm* — Nutter McClennen & Fish LLP

(57) ABSTRACT

Various methods and devices are provided for connecting spinal fixation elements, such as spinal rods, implanted in a patient's spinal column. In particular, various spinal cross connectors are provided for connecting to one or more spinal fixation elements implanted in a patient's spine. The cross connectors can have a variety of configurations, including a fixed or adjustable length, as well as various features that allow certain portions of the cross connectors to be angularly oriented.

13 Claims, 15 Drawing Sheets

(56) References Cited

U.S. PATENT DOCUMENTS

| | | |
|---|---|---|
| 3,499,222 A | 3/1970 | Linkow et al. |
| 3,752,203 A | 8/1973 | Hill, Jr. |
| 4,011,602 A | 3/1977 | Rybicki et al. |
| 4,085,744 A | 4/1978 | Lewis et al. |
| 4,179,905 A | 12/1979 | Schultenkamper |
| 4,289,124 A | 9/1981 | Zickel |
| 4,404,967 A | 9/1983 | Bacal et al. |
| 4,411,259 A | 10/1983 | Drummond |
| 4,611,580 A | 9/1986 | Wu |
| 4,611,581 A | 9/1986 | Steffee |
| 4,611,582 A | 9/1986 | Duff |
| 4,641,636 A | 2/1987 | Cotrel |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,743,260 A | 5/1988 | Burton |
| 4,759,769 A | 7/1988 | Hedman et al. |
| 4,763,644 A | 8/1988 | Webb |
| 4,771,767 A | 9/1988 | Steffee |
| 4,773,402 A | 9/1988 | Asher et al. |
| 4,805,602 A | 2/1989 | Puno et al. |
| 4,815,453 A | 3/1989 | Cotrel |
| 4,887,595 A | 12/1989 | Heinig et al. |
| 4,913,134 A | 4/1990 | Luque |
| 4,950,269 A | 8/1990 | Gaines, Jr. |
| 4,957,495 A | 9/1990 | Kluger |
| 5,002,542 A | 3/1991 | Frigg |
| 5,005,562 A | 4/1991 | Cotrel |
| 5,010,879 A | 4/1991 | Moriya et al. |
| 5,024,213 A | 6/1991 | Asher et al. |
| 5,030,220 A | 7/1991 | Howland |
| 5,067,955 A | 11/1991 | Cotrel |
| 5,084,049 A | 1/1992 | Asher et al. |
| 5,092,866 A | 3/1992 | Breard et al. |
| 5,092,893 A | 3/1992 | Smith |
| 5,102,412 A | 4/1992 | Rogozinski |
| 5,113,685 A | 5/1992 | Asher et al. |
| 5,116,334 A | 5/1992 | Cozad et al. |
| 5,120,171 A | 6/1992 | Lasner |
| 5,127,912 A | 7/1992 | Ray et al. |
| 5,129,899 A | 7/1992 | Small et al. |
| 5,129,900 A | 7/1992 | Asher et al. |
| 5,133,716 A | 7/1992 | Plaza |
| 5,147,359 A | 9/1992 | Cozad et al. |
| 5,147,360 A | 9/1992 | Dubousset |
| 5,154,718 A | 10/1992 | Cozad et al. |
| 5,176,678 A | 1/1993 | Tsou |
| 5,176,680 A | 1/1993 | Vignaud et al. |
| 5,190,543 A | 3/1993 | Schlapfer |
| 5,207,678 A | 5/1993 | Harms et al. |
| 5,234,431 A | 8/1993 | Keller |
| 5,242,443 A | 9/1993 | Kambin |
| 5,261,907 A | 11/1993 | Vignaud et al. |
| 5,261,913 A | 11/1993 | Marnay |
| 5,275,600 A | 1/1994 | Allard et al. |
| 5,282,801 A | 2/1994 | Sherman |
| 5,282,863 A | 2/1994 | Burton |
| 5,304,177 A | 4/1994 | Pennig |
| 5,306,275 A | 4/1994 | Bryan |
| 5,312,405 A | 5/1994 | Korotko et al. |
| 5,330,473 A | 7/1994 | Howland |
| 5,334,203 A | 8/1994 | Wagner |
| 5,360,431 A | 11/1994 | Puno et al. |
| 5,366,455 A | 11/1994 | Dove et al. |
| 5,368,594 A | 11/1994 | Martin et al. |
| 5,387,213 A | 2/1995 | Breard et al. |
| 5,395,370 A | 3/1995 | Muller et al. |
| 5,397,363 A | 3/1995 | Gelbard |
| 5,403,316 A | 4/1995 | Ashman |
| 5,415,661 A | 5/1995 | Holmes |
| 5,419,522 A | 5/1995 | Luecke et al. |
| 5,423,818 A | 6/1995 | Van Hoeck et al. |
| 5,437,671 A | 8/1995 | Lozier et al. |
| 5,439,463 A | 8/1995 | Lin |
| 5,454,812 A | 10/1995 | Lin |
| 5,458,642 A | 10/1995 | Beer et al. |
| 5,470,333 A | 11/1995 | Ray |
| 5,474,086 A | 12/1995 | McCormick et al. |
| 5,476,462 A | 12/1995 | Allard et al. |
| 5,487,742 A | 1/1996 | Cotrel |
| 5,496,321 A | 3/1996 | Puno et al. |
| 5,498,263 A | 3/1996 | DiNello et al. |
| 5,514,132 A | 5/1996 | Csernatony et al. |
| 5,522,816 A | 6/1996 | Dinello et al. |
| 5,527,314 A | 6/1996 | Brumfield et al. |
| 5,531,745 A | 7/1996 | Ray |
| 5,534,002 A | 7/1996 | Brumfield et al. |
| 5,540,688 A | 7/1996 | Navas |
| 5,549,607 A | 8/1996 | Olson et al. |
| 5,556,431 A | 9/1996 | Buttner-Janz |
| 5,562,662 A | 10/1996 | Brumfield et al. |
| 5,562,663 A | 10/1996 | Wisnewski et al. |
| 5,562,737 A | 10/1996 | Graf |
| 5,571,191 A | 11/1996 | Fitz |
| 5,582,612 A | 12/1996 | Lin |
| 5,584,831 A | 12/1996 | McKay |
| 5,586,983 A | 12/1996 | Sanders et al. |
| 5,591,165 A | 1/1997 | Jackson |
| 5,601,552 A | 2/1997 | Cotrel |
| 5,609,592 A | 3/1997 | Brumfield et al. |
| 5,616,142 A | 4/1997 | Yuan et al. |
| 5,620,444 A | 4/1997 | Assaker |
| 5,624,442 A | 4/1997 | Mellinger et al. |
| 5,630,816 A | 5/1997 | Kambin |
| 5,651,789 A | 7/1997 | Cotrel |
| 5,662,653 A | 9/1997 | Hattori et al. |
| 5,667,506 A | 9/1997 | Sutterlin |
| 5,667,507 A | 9/1997 | Corin et al. |
| 5,669,910 A | 9/1997 | Korhonen et al. |
| 5,672,175 A | 9/1997 | Martin |
| 5,676,703 A | 10/1997 | Gelbard |
| 5,683,393 A | 11/1997 | Ralph |
| 5,688,272 A | 11/1997 | Montague et al. |
| 5,700,292 A | 12/1997 | Margulies |
| 5,704,936 A | 1/1998 | Mazel |
| 5,707,372 A | 1/1998 | Errico et al. |
| 5,709,684 A | 1/1998 | Errico et al. |
| 5,709,685 A | 1/1998 | Dombrowski et al. |
| 5,716,355 A | 2/1998 | Jackson et al. |
| 5,743,907 A | 4/1998 | Asher et al. |
| 5,743,911 A | 4/1998 | Cotrel |
| 5,752,955 A | 5/1998 | Errico |
| 5,776,135 A | 7/1998 | Errico et al. |
| 5,876,403 A | 3/1999 | Shitoto |
| 5,885,284 A | 3/1999 | Errico et al. |
| 5,899,903 A | 5/1999 | Cotrel |
| RE36,221 E | 6/1999 | Breard et al. |
| 5,928,232 A | 7/1999 | Howland et al. |
| 5,934,818 A | 8/1999 | Schmitt et al. |
| 5,937,363 A | 8/1999 | Saidi et al. |
| 5,947,966 A | 9/1999 | Drewry et al. |
| 5,961,516 A | 10/1999 | Graf |
| 5,980,521 A | 11/1999 | Montague et al. |
| 5,980,523 A | 11/1999 | Jackson |
| 5,989,250 A | 11/1999 | Wagner et al. |
| 5,989,251 A | 11/1999 | Nichols |
| 6,063,089 A | 5/2000 | Errico et al. |
| RE36,758 E | 6/2000 | Fitz |
| 6,083,226 A | 7/2000 | Fiz |
| 6,110,173 A | 8/2000 | Thomas, Jr. |
| 6,113,600 A | 9/2000 | Drummond et al. |
| 6,126,660 A | 10/2000 | Dietz |
| 6,132,464 A | 10/2000 | Martin |
| 6,136,003 A | 10/2000 | Hoeck et al. |
| 6,139,548 A | 10/2000 | Errico |
| 6,171,311 B1 | 1/2001 | Richelsoph |
| 6,217,578 B1 | 4/2001 | Crozet et al. |
| 6,234,705 B1 | 5/2001 | Troxell |
| 6,238,396 B1 | 5/2001 | Lombardo |
| 6,264,658 B1 | 7/2001 | Lee et al. |
| 6,267,764 B1 | 7/2001 | Elberg |

(56) References Cited

U.S. PATENT DOCUMENTS

| | | |
|---|---|---|
| 6,273,888 B1 | 8/2001 | Justis |
| 6,283,967 B1 | 9/2001 | Troxell et al. |
| 6,287,309 B1 | 9/2001 | Baccelli et al. |
| 6,302,882 B1 | 10/2001 | Lin et al. |
| 6,315,779 B1 | 11/2001 | Morrison et al. |
| 6,328,741 B1 * | 12/2001 | Richelsoph .................. 606/252 |
| 6,355,038 B1 | 3/2002 | Pisharodi |
| 6,402,751 B1 | 6/2002 | Hoeck et al. |
| 6,413,257 B1 | 7/2002 | Lin et al. |
| 6,413,258 B1 | 7/2002 | Bernhardt, Jr. |
| 6,419,703 B1 | 7/2002 | Fallin et al. |
| 6,432,108 B1 | 8/2002 | Burgess et al. |
| 6,440,169 B1 | 8/2002 | Elberg et al. |
| 6,524,310 B1 | 2/2003 | Lombardo et al. |
| 6,551,318 B1 | 4/2003 | Stahurski |
| 6,554,831 B1 | 4/2003 | Rivard et al. |
| 6,554,832 B2 | 4/2003 | Shluzas |
| 6,565,605 B2 | 5/2003 | Goble et al. |
| 6,579,319 B2 | 6/2003 | Goble et al. |
| 6,595,992 B1 | 7/2003 | Wagner et al. |
| 6,602,253 B2 | 8/2003 | Richelsoph et al. |
| 6,610,091 B1 | 8/2003 | Reiley |
| 6,616,668 B2 | 9/2003 | Altarac et al. |
| 6,616,669 B2 | 9/2003 | Ogilvie et al. |
| 6,641,583 B2 | 11/2003 | Shluzas et al. |
| 6,645,207 B2 | 11/2003 | Dixon et al. |
| 6,669,729 B2 | 12/2003 | Chin |
| 6,673,073 B1 | 1/2004 | Schafer |
| 6,689,133 B2 | 2/2004 | Morrison et al. |
| 6,699,248 B2 | 3/2004 | Jackson |
| 6,702,814 B2 | 3/2004 | Walulik et al. |
| 6,736,817 B2 | 5/2004 | Troxell et al. |
| 6,752,807 B2 | 6/2004 | Lin et al. |
| 6,761,721 B2 | 7/2004 | Burgess et al. |
| 6,802,844 B2 | 10/2004 | Ferree |
| 6,811,567 B2 | 11/2004 | Reiley |
| 6,872,208 B1 * | 3/2005 | McBride et al. ............. 606/86 A |
| 6,875,211 B2 | 4/2005 | Nichols et al. |
| 6,887,241 B1 | 5/2005 | McBride et al. |
| 6,958,066 B2 | 10/2005 | Richelsoph et al. |
| 6,960,212 B2 | 11/2005 | Richelsoph et al. |
| 7,011,685 B2 | 3/2006 | Arnin et al. |
| 7,029,474 B2 | 4/2006 | Richelsoph et al. |
| 7,066,938 B2 | 6/2006 | Slivka et al. |
| 7,645,294 B2 | 1/2010 | Kalfas et al. |
| 7,717,938 B2 | 5/2010 | Kim et al. |
| 7,717,939 B2 | 5/2010 | Ludwig et al. |
| 7,717,940 B2 | 5/2010 | Woods et al. |
| 7,879,074 B2 | 2/2011 | Kwak et al. |
| 7,967,845 B2 | 6/2011 | Lauryssen et al. |
| 8,192,471 B2 | 6/2012 | Ludwig et al. |
| 8,361,117 B2 | 1/2013 | Michielli et al. |
| 8,372,119 B2 | 2/2013 | Kim et al. |
| 8,556,937 B2 | 10/2013 | Ludwig et al. |
| 8,591,550 B2 | 11/2013 | Ludwig et al. |
| 2002/0007183 A1 | 1/2002 | Lee et al. |
| 2002/0032442 A1 | 3/2002 | Altarac et al. |
| 2002/0052603 A1 | 5/2002 | Nichols et al. |
| 2002/0065557 A1 | 5/2002 | Goble et al. |
| 2002/0072800 A1 | 6/2002 | Goble et al. |
| 2002/0095154 A1 | 7/2002 | Atkinson et al. |
| 2002/0111625 A1 | 8/2002 | Richelsoph et al. |
| 2002/0123806 A1 | 9/2002 | Reiley |
| 2002/0133155 A1 | 9/2002 | Ferree |
| 2002/0138077 A1 | 9/2002 | Ferree |
| 2002/0143327 A1 | 10/2002 | Shluzas |
| 2002/0143330 A1 | 10/2002 | Shluzas |
| 2002/0151892 A1 | 10/2002 | Walulik et al. |
| 2002/0169448 A1 | 11/2002 | Vanacker |
| 2003/0004572 A1 | 1/2003 | Goble et al. |
| 2003/0018334 A1 | 1/2003 | Richelsoph et al. |
| 2003/0023244 A1 | 1/2003 | Richelsoph et al. |
| 2003/0028192 A1 | 2/2003 | Schar et al. |
| 2003/0028250 A1 | 2/2003 | Reiley et al. |
| 2003/0045874 A1 | 3/2003 | Thomas |
| 2003/0050640 A1 | 3/2003 | Lee et al. |
| 2003/0055427 A1 | 3/2003 | Graf |
| 2003/0083657 A1 | 5/2003 | Drewry et al. |
| 2003/0109880 A1 | 6/2003 | Shirado et al. |
| 2003/0114853 A1 | 6/2003 | Burgess et al. |
| 2003/0135277 A1 | 7/2003 | Bryan et al. |
| 2003/0153912 A1 | 8/2003 | Graf |
| 2003/0153914 A1 | 8/2003 | Oribe et al. |
| 2003/0153917 A1 | 8/2003 | Richelsoph et al. |
| 2003/0171749 A1 | 9/2003 | Le Couedic et al. |
| 2003/0171750 A1 | 9/2003 | Chin |
| 2003/0191470 A1 | 10/2003 | Ritland |
| 2003/0191532 A1 | 10/2003 | Goble et al. |
| 2003/0212398 A1 | 11/2003 | Jackson |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0006391 A1 | 1/2004 | Reiley |
| 2004/0039385 A1 | 2/2004 | Mazda et al. |
| 2004/0049188 A1 | 3/2004 | Slivka et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0087949 A1 | 5/2004 | Bono et al. |
| 2004/0111154 A1 | 6/2004 | Reiley |
| 2004/0116927 A1 | 6/2004 | Graf |
| 2004/0116928 A1 | 6/2004 | Young et al. |
| 2004/0127904 A1 | 7/2004 | Konieczynski et al. |
| 2004/0133203 A1 * | 7/2004 | Young et al. .................... 606/61 |
| 2004/0143264 A1 | 7/2004 | McAfee |
| 2004/0167526 A1 | 8/2004 | Jackson |
| 2004/0172024 A1 | 9/2004 | Gorek |
| 2004/0176765 A1 | 9/2004 | Troxell et al. |
| 2004/0186474 A1 | 9/2004 | Matthis et al. |
| 2004/0186475 A1 | 9/2004 | Falahee |
| 2004/0236328 A1 | 11/2004 | Paul et al. |
| 2004/0236329 A1 | 11/2004 | Panjabi |
| 2004/0254574 A1 | 12/2004 | Morrison et al. |
| 2004/0260287 A1 | 12/2004 | Ferree |
| 2005/0010222 A1 | 1/2005 | Cordaro |
| 2005/0033431 A1 | 2/2005 | Gordon et al. |
| 2005/0033432 A1 | 2/2005 | Gordon et al. |
| 2005/0033439 A1 | 2/2005 | Gordon et al. |
| 2005/0080416 A1 | 4/2005 | Ryan et al. |
| 2005/0090821 A1 | 4/2005 | Berrevoets et al. |
| 2005/0090823 A1 | 4/2005 | Bartimus |
| 2005/0101954 A1 | 5/2005 | Simonson |
| 2005/0101956 A1 | 5/2005 | Simonson |
| 2005/0102028 A1 | 5/2005 | Arnin et al. |
| 2005/0113831 A1 | 5/2005 | Franck et al. |
| 2005/0113927 A1 | 5/2005 | Malek |
| 2005/0119657 A1 | 6/2005 | Goldsmith |
| 2005/0177152 A1 | 8/2005 | Baynham et al. |
| 2005/0192569 A1 | 9/2005 | Nichols et al. |
| 2005/0228326 A1 | 10/2005 | Kalfas et al. |
| 2005/0228376 A1 | 10/2005 | Boomer et al. |
| 2005/0228377 A1 | 10/2005 | Chao et al. |
| 2006/0058789 A1 * | 3/2006 | Kim et al. ....................... 606/61 |
| 2006/0058791 A1 | 3/2006 | Broman et al. |
| 2006/0064091 A1 | 3/2006 | Ludwig et al. |
| 2006/0064093 A1 | 3/2006 | Thramann et al. |
| 2006/0142759 A1 | 6/2006 | Arnin et al. |
| 2006/0200130 A1 | 9/2006 | Hawkins et al. |
| 2006/0241757 A1 | 10/2006 | Anderson |
| 2006/0271045 A1 * | 11/2006 | Hubbard et al. ................ 606/61 |
| 2006/0271051 A1 | 11/2006 | Berrevoets et al. |
| 2007/0043356 A1 | 2/2007 | Timm et al. |
| 2007/0049936 A1 | 3/2007 | Colleran et al. |
| 2007/0073289 A1 | 3/2007 | Kwak et al. |
| 2007/0073396 A1 | 3/2007 | Arnin |

(56) References Cited

U.S. PATENT DOCUMENTS

| | | |
|---|---|---|
| 2008/0109039 A1 | 5/2008 | Michielli et al. |
| 2009/0036928 A1 | 2/2009 | Kim et al. |
| 2010/0036420 A1 | 2/2010 | Kalfas et al. |
| 2010/0191289 A1 | 7/2010 | Ludwig et al. |
| 2012/0101529 A1 | 4/2012 | Ludwig et al. |
| 2012/0283780 A1 | 11/2012 | Ludwig et al. |
| 2013/0131727 A1 | 5/2013 | Kim et al. |
| 2014/0012320 A1 | 1/2014 | Ludwig et al. |

FOREIGN PATENT DOCUMENTS

| | | |
|---|---|---|
| DE | 3639810 A1 | 5/1988 |
| DE | 4330837 A1 | 3/1995 |
| EP | 0 128 058 A1 | 12/1984 |
| EP | 0 242 708 | 10/1987 |
| EP | 0 669 109 A1 | 8/1995 |
| EP | 0 820 722 A1 | 1/1998 |
| EP | 0 878 170 A2 | 11/1998 |
| EP | 0 956 829 A2 | 11/1999 |
| EP | 1 295 566 A1 | 3/2003 |
| FR | 2615095 | 11/1988 |
| FR | 2624720 A1 | 6/1989 |
| FR | 2645427 A1 | 10/1990 |
| FR | 2697743 A1 | 5/1994 |
| FR | 2714590 A1 | 7/1995 |
| FR | 2795622 A1 | 1/2001 |
| FR | 2813782 A1 | 3/2002 |
| FR | 2816195 A1 | 5/2002 |
| GB | 167228 A | 7/1921 |
| GB | 2173104 A | 10/1986 |
| GB | 2208476 A | 4/1989 |
| JP | 11-244299 A | 9/1999 |
| JP | 2000-033091 A | 2/2000 |
| JP | 2004-073855 A | 3/2004 |
| JP | 2004-518482 A | 6/2004 |
| SU | 286136 | 11/1970 |
| SU | 1823791 A3 | 6/1993 |
| WO | 87/00160 A1 | 1/1987 |
| WO | 90/04948 A1 | 5/1990 |
| WO | 91/16020 A1 | 10/1991 |
| WO | 95/13754 A1 | 5/1995 |
| WO | 99/09903 A1 | 3/1999 |
| WO | 00/57801 A1 | 10/2000 |
| WO | 00/59387 A1 | 10/2000 |
| WO | 01/01872 A1 | 1/2001 |
| WO | 01/24718 A1 | 4/2001 |
| WO | 01/45576 A1 | 6/2001 |
| WO | 01/47425 A1 | 7/2001 |
| WO | 02/17803 A2 | 3/2002 |
| WO | 02/30307 A2 | 4/2002 |
| WO | 02/43603 A1 | 6/2002 |
| WO | 02/102259 A2 | 12/2002 |
| WO | 03/007828 A1 | 1/2003 |
| WO | 03/009737 A1 | 2/2003 |
| WO | 03/063715 A1 | 8/2003 |
| WO | 2004/024011 A1 | 3/2004 |
| WO | 2004/034916 A1 | 4/2004 |

OTHER PUBLICATIONS

Lim, et al., "Biomechanics of Transfixation in Pedicle Screw Instrumentation", Spine, vol. 21, No. 19, pp. 2224-2229, 1996.

Betz, Randall R. et al., DePuy AcroMed Brochure, "Fronterior Anterior Deformity System," Surgical Technique, 21 pages, Aug. 2002.

DePuy AcroMed, "CrossOver CrossConnector" brochure, Apr. 2003.

Dick et al., "Mechanical Evaluation of Cross-Link Designs in Rigid Pedicle Screw Systems", Spine, vol. 22, No. 4, pp. 370-375, 1997.

Kaneda, Kiyoshi et al., DePuy AcroMed Brochure "Kaneda SR Anterior Spinal System," Surgical Technique, pp. 1-11, 1999.

DePuy AcroMed, "Modular Cross Connector (MCC)" brochure, 2000.

Carson et al., "Internal Forces and Moments in Transpecular Spine Instrumentation", Spine, vol. 15, No. 9, pp. 893-901 (1999).

Hitodo, H., "Bone Fixing Device," Patent Abstracts of Japan; Sep. 14, 1999, No. 14; Abstract of JP 11244299.

Office Action dated Apr. 20, 2009 issued in U.S. Appl. No. 10/813,904.

European Search Report EP 02257087.3 dated Feb. 19, 2003.

Expedium SFX Cross Connector System Surgical Technique. Brochure, print date Nov. 2006.

International Search Report and Written Opinion in Pat. App. No. PCT/US07/22505 dated Jul. 11, 2008.

International Search Report from PCT/US2005/010513 dated Nov. 8, 2005, 5 pages.

International Search Report issued for PCT/US06/31000; mailing date Mar. 20, 2008, 4 pages.

Krag, M.H., "Biomechanics of Thorocolumbar Spinal Fixation," Spine, vol. 16, No. 3 Supplement, pp. S84-S99 (1991).

Materials—Biocompatible non-fouling PEO coating for biomaterials, Biomedical Materials, International Newsletters, 1994, HighBeam Research, May 21, 2009 <http://www.highbeam.com>.

Office Action in Australian Pat. App. No. 2007318173 dated Apr. 21, 2010.

Office Action in Canadian Pat. App. No. 2,668,485 dated Nov. 8, 2010.

Ovation™ Polyaxial System by Osteotech Inc. (author unknown), description downloaded from http://www.osteotech.com/prodpoly2.htm; pp. 1-6; (Oct. 28, 2003).

SFX Snap-Fit Cross Connector 510(k) Summary, approval date Sep. 11, 2006.

European Office Action for Application No. 07852912.0 issued Mar. 27, 2014 (5 Pages).

\* cited by examiner

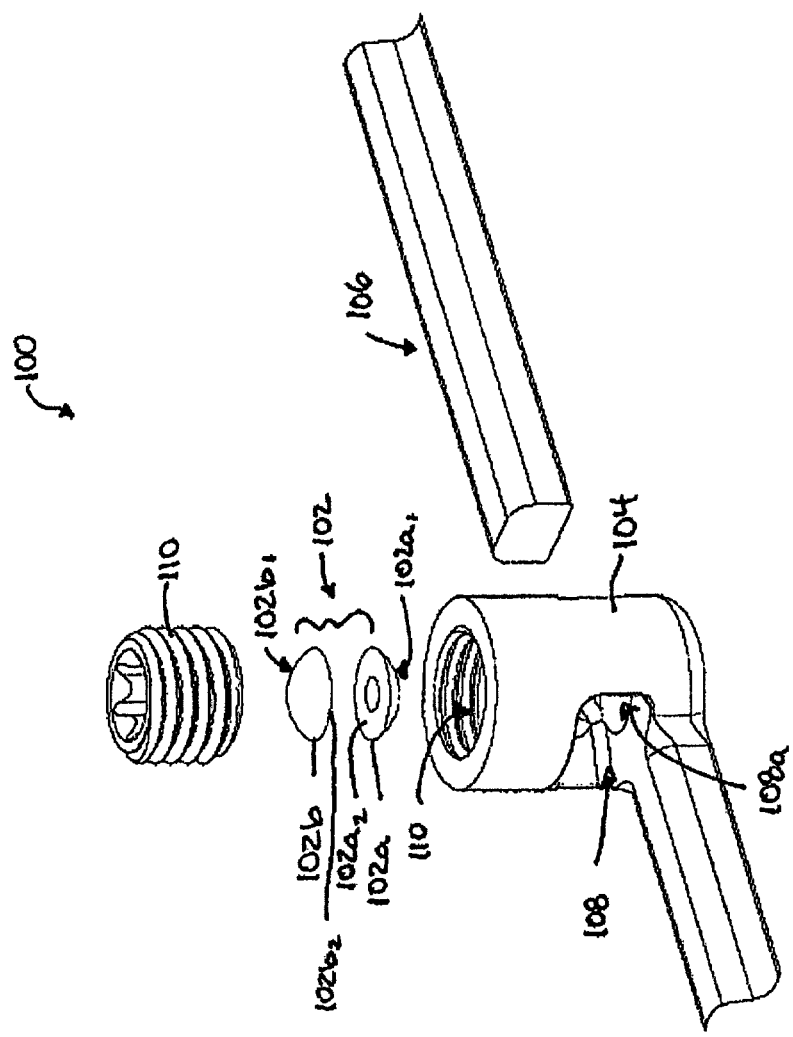

FIG. 9A
FIG. 9B
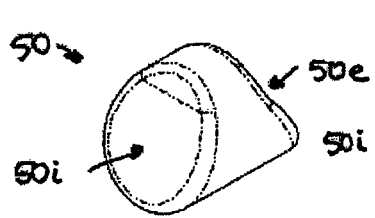
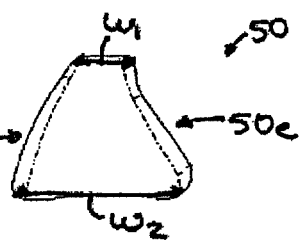
FIG. 10A
FIG. 10B
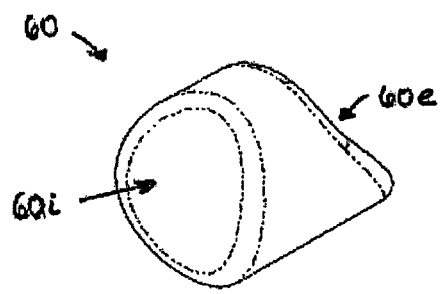
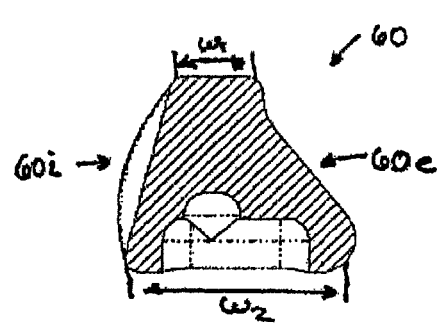
FIG. 11A
FIG. 11B
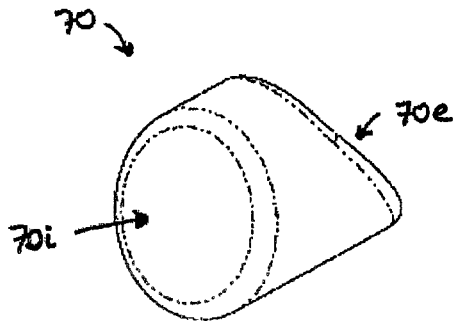
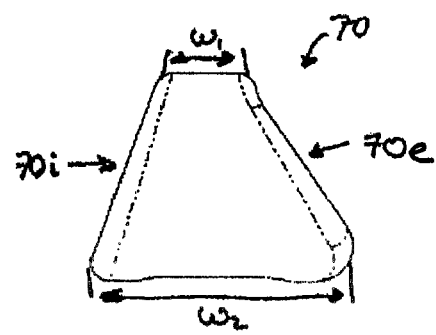

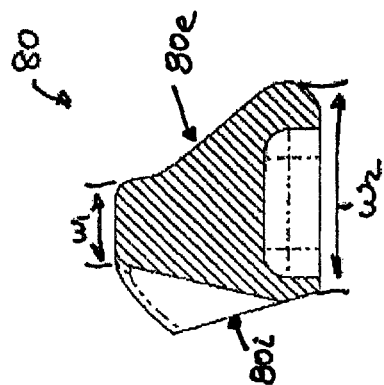
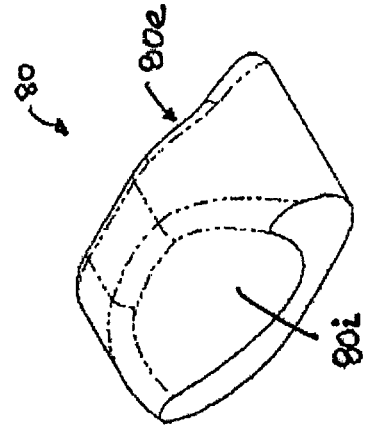
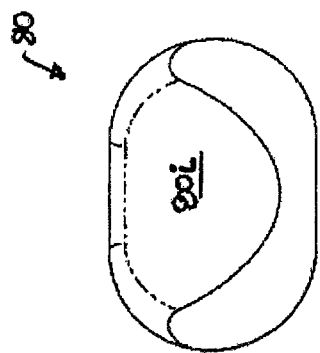
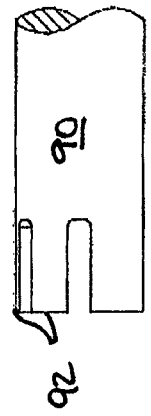
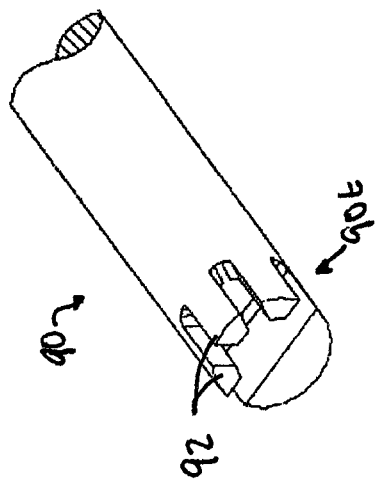

SPINAL CROSS CONNECTORS

CROSS-REFERENCE TO RELATED APPLICATIONS

The present application is a continuation of U.S. patent application Ser. No. 11/557,699 filed on Nov. 8, 2006 and entitled "Spinal Cross Connectors," which is hereby incorporated by reference in its entirety.

FIELD OF THE INVENTION

The present invention relates to spinal fixation devices, and in particular to a cross connector for connecting spinal fixation elements, such as spinal fixation rods, implanted in a patient's spinal system.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site, and once installed, the rods hold the vertebrae in a desired spatial relationship, either until desired healing or spinal fusion has taken place, or for some longer period of time.

Spinal cross connectors are often used in conjunction with spinal fixation devices to provide additional stability to the devices. For example, it has been found that when a pair of spinal rods are fastened in parallel on either side of the spinous process, the assembly can be significantly strengthened by using a cross connector to bridge the pair of spinal rods. The connectors are typically in the form of a rod having a clamp formed on each end thereof for mating with a spinal rod.

While current spinal cross connectors have proven effective, difficulties have been encountered in mounting the cross connectors, and maintaining them in a desired position and orientation with respect to the spinal rod, or other spinal fixation device to which they are attached. In particular, the clamp assemblies often consist of several parts which make surgical application tedious, and which can also increase the manufacturing costs. Since the cross connector is often applied as the last step in a lengthy surgical procedure, ease of application is paramount. Fixation of the cross connector to spinal rods can also be difficult where the rods are not parallel to one another (diverging/converging with respect to one another), or out of plane with each other.

Accordingly, a need exists for improved spinal cross connectors that can be easily installed and that securely mate to and connect spinal fixation devices.

SUMMARY OF THE INVENTION

The present invention generally provides various methods and devices for connecting spinal fixation elements, such as spinal rods, implanted in a patient's spinal column. In one embodiment, a spinal cross connector is provided having a first connector element for engaging a first spinal fixation element, and a second connector element for engaging a second spinal fixation element. The first connector element can have a female member, and the second connector element can have a male member that is receivable within the female member such that the male member is adjustably slidable within the female member along a longitudinal axis of the male member, rotatable about the longitudinal axis within the female member, and pivotable within the female member such that the longitudinal axis can be angularly oriented relative to a longitudinal axis of the first connector element. The cross connector can also include a fastening element that is adapted to be disposed within the female member to engage and lock the male member in a fixed position relative to the female member.

The male and female members of the cross connector can have a variety of configurations, but in one embodiment the female member can be in the form of a housing having a first opening formed therethrough for receiving the male member, and second opening formed therethrough that is in communication with the first opening and that is configured to receive the fastening element. The first opening in the female member can include opposed portions that increase in width from a substantial mid-portion of the first opening such that the opposed portions allow the male member to pivot within the female member. The male member can be in the form of a generally elongate cylindrical shaft. In one exemplary embodiment, the male member can be disposed through the female member and the male member can include a retaining element formed on a terminal end thereof that is adapted to prevent removal of the male member from the female member. The fastening element can also optionally include a retaining element formed thereon that is adapted to prevent removal of the fastening element from the female member.

In another exemplary embodiment, when the male member and the fastening element are disposed within the female member, the male and female members can have first and second points of contact therebetween and the male member and the fastening element can have one point of contact therebetween. The first and second points of contact between the male and female members can be spaced a distance apart from one another.

The spinal cross connector can also include first and second engagement elements slidably disposed within the first and second connector elements, and first and second locking mechanisms receivable within the first and second connector elements and adapted to slidably move the first and second engagement elements to cause the first and second engagement elements to engage and lock a spinal fixation element within first and second recesses formed in the first and second connector elements. The cross connector can include other features as well, such as a bend zone formed in at least one of the first and second connector elements.

In yet another embodiment, a spinal cross connector is provided having first and second connector elements for engaging a spinal fixation element. The first connector element can have a female member, and the second connector element can have a male member that is receivable within the female member. The cross connector can also include a fastening element that is adapted to be disposed within the female member to lock the male member in a fixed position relative to the female member. The fastening element can be, for example, a threaded member adapted to mate with corresponding threads formed within the female member. The cross connector can also include a first insert that is adapted to be disposed within the female member and to be positioned between the male member and the female member, and a second insert that is adapted to be disposed within the female member and to be positioned between the fastener and the male member. In an exemplary embodiment, the first and second inserts are adapted to allow the male member to pivot within the female member such that a longitudinal axis of the second connector element can be angularly oriented relative to a longitudinal axis of the first connector element. More preferably, the male member is (i) adjustably slidable within the female member along a longitudinal axis of the male member, (ii) rotatable about the longitudinal axis within the female member, and (iii) pivotable within the female member such that the longitudinal axis can be angularly oriented relative to a longitudinal axis of the first connector element.

The first and second inserts can have a variety of shapes and sizes, but in one embodiment each insert has a substantially hemispherical shape. The male member can include opposed planar surfaces that rest between planar surfaces on the first and second inserts when the male member and first and second inserts are disposed within the female member. The female member can be in the form of a housing having a first opening formed therethrough for receiving the male member, and a second opening formed therethrough for receiving the fastening element. The first opening can include a concavity formed therein and adapted to polyaxially seat the first insert and the fastening element can include a concavity formed therein and adapted to polyaxially seat the second insert.

In another embodiment, the first connector element can have a generally elongate shaft with a first terminal end having a recess formed therein for receiving a spinal fixation element and a second terminal end having the female member formed thereon, and the second connector element can have a generally elongate shaft with a first terminal end having a recess formed therein for receiving a spinal fixation element and a second terminal end that forms the male member.

In yet another embodiment, a spinal cross connector is provided having an elongate member with a first end with a first recess formed therein that is configured to receive a spinal fixation element, and an opposed second end with a second recess formed therein that is configured to receive a spinal fixation element. The cross connector can also include first and second engagement elements disposed within the elongate member, and first and second locking mechanisms disposable within first and second openings formed in the first and second ends. The first and second openings can be positioned such that the first and second recesses are located between the first and second openings, and the first and second locking mechanisms can be adapted to move the first and second engagement elements to cause the first and second engagement elements to engage and lock first and second spinal fixation elements within the first and second recesses. In an exemplary embodiment, the elongate member can include opposed top and bottom surfaces, and the first and second recesses can be formed in the bottom surface and the first and second openings can be formed in the top surface. In other embodiments, the first and second engagement elements can be slidably disposed within the elongate member, and the first and second locking mechanisms can be adapted to slidably move the first and second engagement elements. In yet another embodiment, the first and second openings can have longitudinal axes that extend substantially perpendicular to a longitudinal axis of the elongate member.

In other aspects, a spinal cross connector is provided having an elongate body with opposed first and second ends and opposed top and bottom surfaces. First and second recesses are formed in the bottom surface adjacent to the first and second ends of the elongate body. The first and second recesses are oriented to enable the elongate body to be simultaneously top-loaded onto first and second spinal fixation elements. The cross connector can also include first and second bores formed in the top surface of the elongate body and effective to receive first and second locking mechanisms for locking first and second spinal fixation elements within the first and second recesses. The first and second bores can have longitudinal axes that are substantially parallel to one another and that are substantially parallel to an axis of loading the elongate body onto first and second spinal fixation elements. In an exemplary embodiment, the first and second recesses are in the form of substantially concave cavities formed in the bottom surface of the elongate body, and having opposed sidewalls that are substantially parallel to one another and substantially parallel to the longitudinal axes of the first and second bores in the elongate member. The cross connector can also include first and second locking mechanisms disposed within the first and second bores and adapted to lock first and second spinal fixation elements within the first and second recesses, and/or first and second engagement elements movably disposed within the elongate body. The first and second locking mechanisms can be effective to move the first and second engagement elements to cause the first and second engagement elements to engage and lock first and second spinal fixation elements within the first and second recesses.

BRIEF DESCRIPTION OF THE DRAWINGS

The invention will be more fully understood from the following detailed description taken in conjunction with the accompanying drawings, in which:

FIG. 2A is an exploded view of another embodiment of a spinal cross connector having male and female members that are adjustable relative to one another;

FIG. 9A is perspective view of one embodiment of an engagement element having a circular cross-section and a convex shaped engaging surface;

FIG. 9B is a side view of the engagement element of FIG. 9A;

FIG. 10A is perspective view of one embodiment of an engagement element having a circular cross-section and a concave engaging surface;

FIG. 10B is a side view of the engagement element of FIG. 10A;

FIG. 11A is perspective view of one embodiment of an engagement element having a circular cross-section and a planar engaging surface;

FIG. 11B is a side view of the engagement element of FIG. 11A;

FIG. 12A is perspective view of one embodiment of an engagement element having an oval-shaped cross section and a concave shaped engaging surface;

FIG. 12B is a perspective view of the engagement element of FIG. 12A;

FIG. 12C is a side view of the engagement element of FIG. 12A;

FIG. 13A is a perspective view of one embodiment of a retaining element having deformable members formed thereon;

FIG. 13B is a side view of the retaining element of FIG. 13A;

DETAILED DESCRIPTION OF THE INVENTION

Figure 1A:
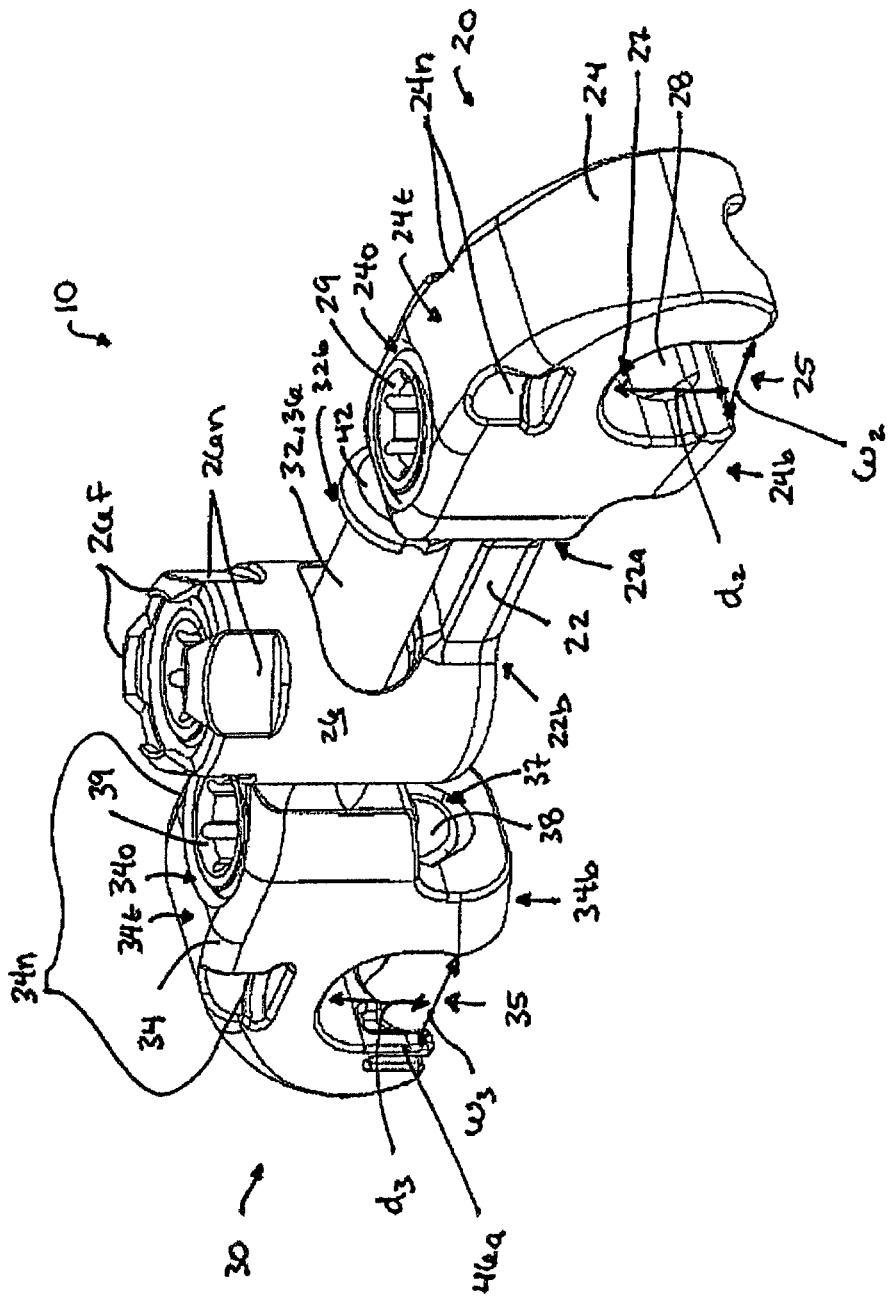
FIG. 1A is a perspective view of one embodiment of a spinal cross connector having male and female members that are adjustable relative to one another.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides various methods and devices for connecting spinal fixation elements, such as spinal rods, implanted in a patient's spinal column. In general, each cross connector is configured to receive and engage at least one, and more preferably two spinal fixation elements. The cross connectors can include various features to facilitate such engagement. In certain exemplary embodiments, the cross connectors can be adjustable to facilitate loading and mating of the cross connector onto two spinal fixation elements implanted in a patient's spinal column. For example, the cross connector can be telescoping, such that a length of the cross connector can be adjusted to accommodate spinal fixation elements positioned at various distances relative to one another. The cross connector can also or alternatively include two members that are axially rotatable and/or pivotable relative to one another, thus accommodating spinal fixation elements residing in different planes and/or extending at various angles (i.e., converging or diverging) relative to one another. In other embodiments, the cross connectors can have a fixed length, and can include other features to facilitate adjustability, such as one or more bend zones. In other embodiments, the cross connectors can be configured to facilitate simultaneous top-loading of the cross connector onto two spinal fixation elements. The spinal cross connectors can also include a variety of other features to facilitate use of the device.

A person skilled in the art will appreciate that while the cross connectors are described herein as being adapted to engage a spinal fixation element, and in particular a spinal fixation rod, the cross connectors can be configured to engage a variety of spinal fixation devices, such as anchors, cables, fixation plates, etc. Moreover, the cross connectors can be configured to engage any number of spinal fixation elements, including a single spinal fixation element. The opposed terminal end of the cross connector can be adapted for other uses. For example, the opposed terminal end of the cross connector can be configured to be fixedly attached to a vertebra. The cross connectors of the present invention can also include any combination of features described and/or illustrated herein, and the cross connectors are not limited to having the configuration shown in the illustrated embodiments.

Figure 1B:
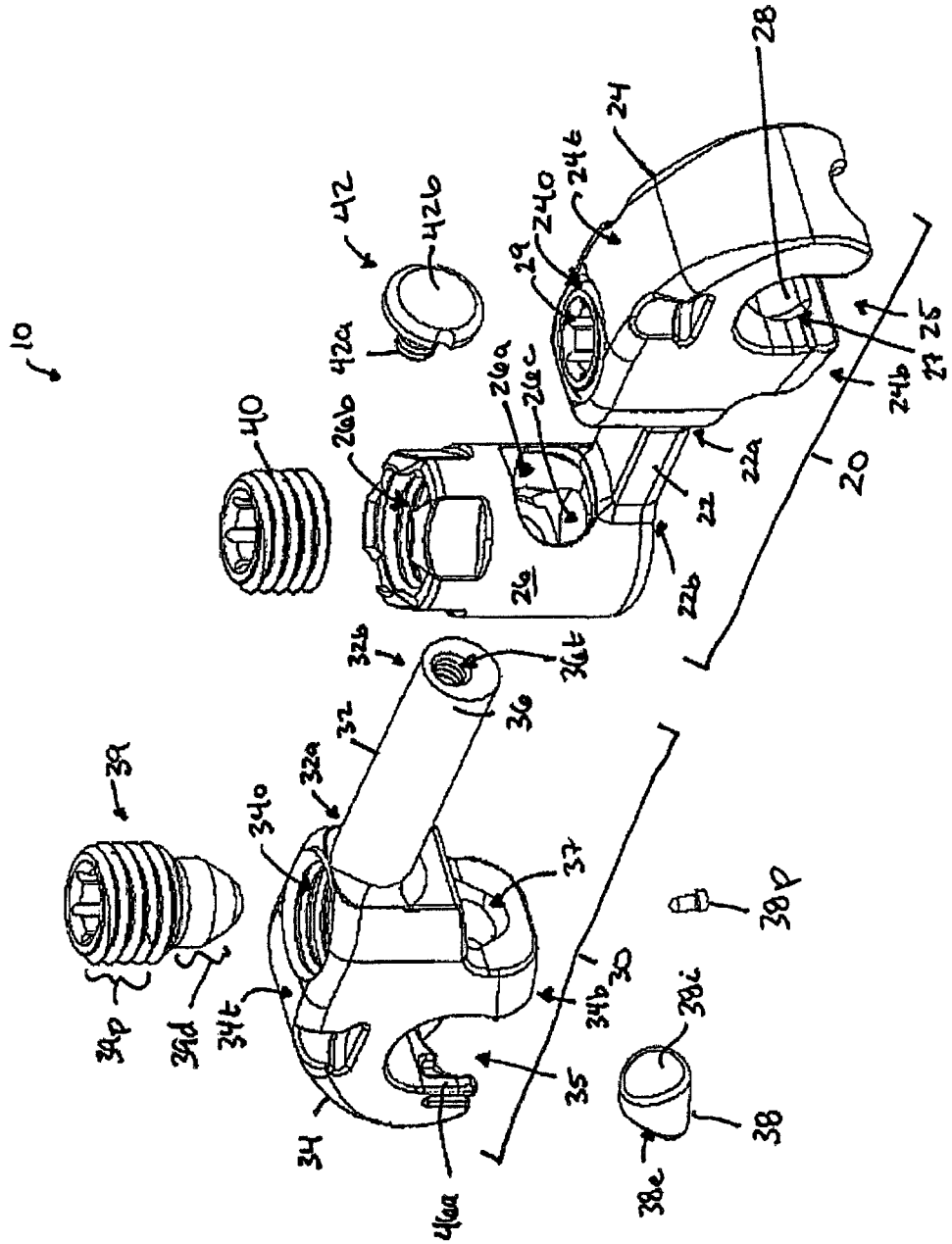
FIG. 1B is an exploded view of the spinal cross connector of FIG. 1A.

FIGS. 1A-1B illustrate one embodiment of a spinal cross connector 10 that can be easily adjusted to allow the cross connector 10 to be applied to two spinal fixation elements oriented in various positions relative to one another. As shown, the cross connector 10 generally includes first and second connector elements 20, 30 that are adjustably matable to one another. The first connector element 20 includes an elongate shaft 22 having a first end 22a with a connector head 24 formed thereon and configured to receive and engage a spinal fixation element, and a second end 22b with a female member 26 formed thereon. The second connector element 30 also includes an elongate shaft 32 with a connector head 34 formed on a first end 32a thereof and configured to receive and engage a spinal fixation element. The second end 32b of the elongate shaft 32, or at least a portion thereof, can form a male member 36 that is configured to be received within the female member 26 of the first connector element 20. In use, as will be explained in more detail below, the male and female members 26, 36 can move relative to one another to facilitate loading the cross connector 10 onto first and second spinal fixation elements implanted in a patient's spine.

The connector head 24, 34 on each connector element 20, 30 can have a variety of configurations, but in one exemplary embodiment each connector head 24, 34 includes a recess 25, 35 formed therein and configured to receive a spinal fixation element, such as a spinal rod. The particular location of the recesses 25, 35 can vary, but in the illustrated embodiment the first and second recesses 25, 35 are formed in a bottom surface 24b, 34b of the connector heads 24, 34. The shape, size, and orientation of each recess 25, 35 can vary depending on the type of spinal fixation element being engaged. In an exemplary embodiment, the cross connector 10 is adapted to connect to two spinal fixation rods. Accordingly, each recess 25, 35 can have a shape that is configured to accommodate a substantially cylindrical spinal rod. In other words, each recess 25, 35 can have a substantially concave shape such that it defines a partially cylindrical cavity. The size of the recesses 25, 35 can also vary depending on the size of the spinal fixation elements. In an exemplary embodiment, each recess 25, 35 has a width $w_2$, $w_3$, measured across the opening of the recess, that is greater than a diameter of a spinal fixation rod disposed therein, and a depth $d_2$, $d_3$ that is greater than a radius of a spinal fixation rod disposed therein. The depth $d_2$, $d_3$ can also be greater than a diameter of the spinal fixation rod, or it can be less than or substantially equal to a diameter of the spinal fixation rod, but preferably each recess 25, 35 is configured to seat a substantial portion of a spinal fixation rod to allow the rod to be firmly locked therein. The recesses 25, 35 can also be oriented to facilitate top-loading of the spinal connector onto two spinal fixation elements disposed within a patient's spinal column. For example, the recesses can have opposed sidewalls that are all substantially parallel to one another. Exemplary recess configurations will be discussed in more detail below with respect to FIGS. 8A and 8B.

The cross connector 10 can also include one or more engagement members, hereinafter referred to as shoes, that are configured to engage a spinal fixation element disposed within the recesses 25, 35. As shown in FIGS. 1A and 1B, the cross connector 10 includes first and second shoes 28, 38 that are slidably disposed within the first and second connector heads 24, 34 and that are positioned adjacent to the first and second recesses 25, 35. The shoes 28, 38 can have a variety of configurations and they can be mated to or disposed within the connector heads 24, 34 using a variety of techniques, but they are preferably effective to move linearly in response to a force applied thereto by a locking mechanism to lock a spinal fixation element within each recess 25, 35. In an exemplary embodiment, each connector head 24, 34 includes first and second receiving cavities 27, 37 formed therein for slidably seating the shoes. In the illustrated embodiment, the first and second cavities 27, 37 are positioned inward of the recesses 25, 35 such that the cavities are located between the recesses 25, 35 when the device 10 is assembled. The cavities 27, 37 can also be spaced a distance apart from the bottom surface 24b, 34b of the connector heads 24, 34 to allow the shoes 28, 38 to be retained within the connector heads 24, 34.

Each cavity 27, 37 can vary in shape and size, but as indicated above in an exemplary embodiment the cavities 27, 37 allow slidable movement of the shoes 28, 38 therein. In particular, each cavity 27, 37 can have a shape that is substantially similar to a shape of the shoes 28, 38, i.e., that is configured to match the contour of each shoe 28, 38, as will be discussed below. The cavities 27, 28 can also extend at a downward angle toward the recesses such that each shoe 28, 38, when moved from within the cavity 27, 28 toward the recess 25, 35, extends in a downward direction. Such a configuration facilitates engagement of the rods disposed within the recesses 25, 35.

Each shoe 28, 38 can also include an internal surface that is configured to contact the locking mechanism, which will be discussed below, and an opposed external surface that faces the recess 25, 35. For reference purposes, only shoe 38 shown in FIG. 1B will be discussed, however both shoes 28, 38 can have the same configuration. The internal and external surfaces 38i, 38e can vary in shape. In an exemplary embodiment, the internal surface 38i has a shape that conforms to the shape of the locking mechanism. For example, the internal surface 38i of the shoe 38 can include a concave recess formed therein, as shown in FIG. 1B, or it can have other shapes such as convex, planar, etc. The concave shape of the internal surface 38i is effective to seat a portion of the locking mechanism. The external surface 38e of the shoe 38 can also have a variety of shapes and sizes, but as illustrated the external surface 38e of the shoe has a substantially planar configuration. The external surfaces, or at least a portion thereof, can also include gripping features, such as ridges, grooves, a surface coating, etc., formed or disposed thereon to engage the rod. Exemplary shoe configurations will be discussed in more detail with respect to FIGS. 9A-12C.

In order to prevent the shoes 28, 38 from falling out of the cavities 27, 37, each connector head 24, 34 can include a retaining mechanism adapted to slidably retain each shoe 28, 38 within each cavity 27, 37. While various retaining mechanisms can be used, in one exemplary embodiment, as shown in FIG. 1B, the cross connector 10 can include first and second pin members (only one pin member 38p is shown) that extend through the bottom surface 24b, 34b of the connector head 24, 34 and into a slot (not shown) formed within a bottom surface of each shoe 28, 38. The slot preferably extends between the internal and external surfaces of the shoes 28, 38 to allow the shoes 28, 38 to slide between the retracted and extended positions. The pin members can be retained within the connector head 24, 34 using various techniques, but preferably the pin members are fixedly mated to the connector head 24, 34 using a press fit or using other techniques known in the art.

Figure 1C:
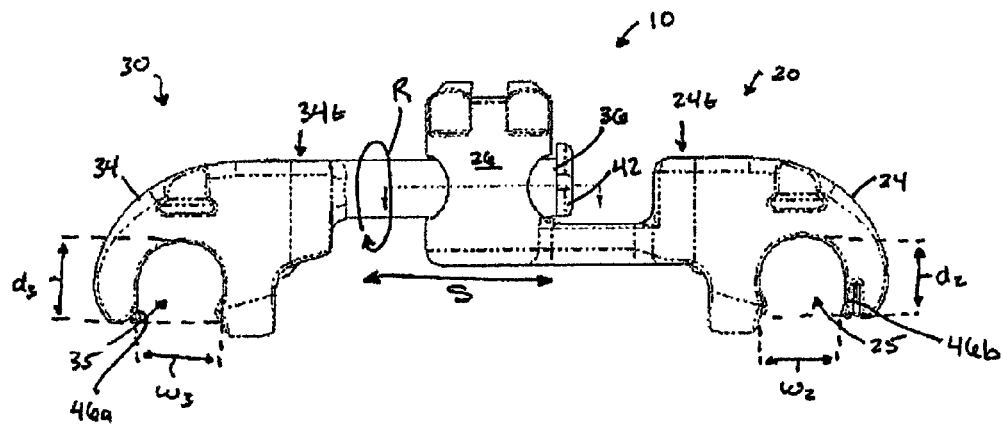
FIG. 1C is a side view of the spinal cross connector of FIG. 1A.

In use, the first and second shoes 28, 38 can be slidably movable between a first retracted position, shown in FIG. 1C, in which the shoes 28, 38 are at least partially or fully disposed within the first and second cavities 27, 37, and a second extended position, as shown in FIGS. 1A and 1B, in which at least a portion of the shoes 28, 38 extend into the recesses 25, 35. The shoes 28, 38 can be moved into the second extended position by inserting a locking mechanism 29, 39 into an opening formed in each connector head 24, 34 such that the locking mechanism 29, 39 applies a force to the shoe 28, 38 to cause the shoe 28, 38 to move linearly and lock a spinal fixation element within the recess 25, 35. The locking mechanisms 29, 39 can have a variety of configurations and they can be receivable within the connector heads 24, 34 at a variety of locations. In the illustrated embodiment, each connector head 24, 34 includes a central opening 24o, 34o formed in a top surface 24t, 34t thereof for receiving the locking mechanism 29, 39. The central openings 24o, 34o preferably extend into and are in communication with the cavities 27, 37 that retain the shoes 28, 38 to allow the locking mechanisms 29, 39 to contact and apply a force to the shoes 28, 38. The locking mechanisms 29, 39, which are receivable within the openings, can have various configurations. In the illustrated embodiment, each locking mechanism 29, 39 has a proximal portion (FIG. 1B illustrates proximal portion 39p on locking mechanism 39) that is adapted to mate to a proximal portion of the opening 24o, 34o, and a distal portion (FIG. 1B illustrates distal portion 39d on locking mechanism 39) that is adapted to apply a force to the shoe 28, 38 to move the shoe 28, 38 into the second extended position. The proximal portion can include threads that are adapted to mate with corresponding threads formed within at least a proximal portion of the opening, or various other mating techniques known in the art can be used. The distal portion of each locking mechanism 29, 39 can also vary in shape and size, but in one exemplary embodiment the distal portion of each locking mechanism 29, 39 is in the form of a shaft or pin-type member. At least a portion of each shaft can taper toward the distal end to facilitate the application of force against the shoe 28, 38. In particular, as previously indicated, the internal surface (internal surface 38i is shown in FIG. 1B) of each shoe 28, 38 can have a concave recess formed therein for seating the tapered shaft. Thus, when the locking mechanisms 29, 39 are threaded into the openings 24o, 34o in the connector heads 24, 34, the tapered shaft of each locking mechanism 29, 39 contacts the concave internal surface of each shoe 28, 38 to force the shoes 28, 38 into the second extended position. The shaft on each locking mechanism 29, 39 can also have a variety of other shapes such as, for example, a spherical shape or cone shape. A person skilled in the art will appreciate that the shape of the distal portion of each locking mechanism can vary depending on the shape of the shoes. The aforementioned shoes and locking mechanism are described in more detail in commonly owned U.S. Publication No. 2006/0058789 entitled "Dual Rod Cross Connectors and Inserts Tools" of Kim et al., which is hereby incorporated by reference in its entirety.

As previously indicated, the cross connector 10 also includes female and male members 26, 36 formed on the second ends 22b, 32b of the elongate shaft 22, 32 of the first and second connector elements 20, 30, respectively. The female and male members 26, 36 can have a variety of configurations, but in the illustrated embodiment the female member 26 is in the form of a housing formed on the second end 22b of the elongate shaft 22 of the first connector element 20, and the male member 36 is merely formed by the elongate shaft 32, or at least a terminal portion thereof, on the second connector element 30. The female and male members 26, 36 mate to form a central portion of the cross connector 10.

Figure 1D:
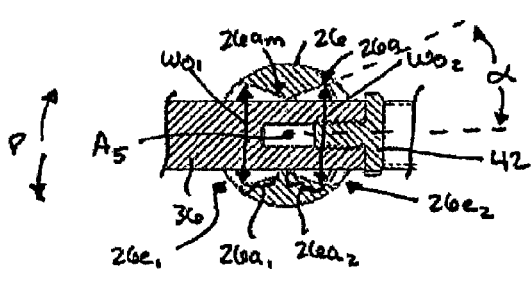
FIG. 1D is a top cross-sectional view of a central portion of the spinal cross connector of FIG. 1A.
Figure 1E:
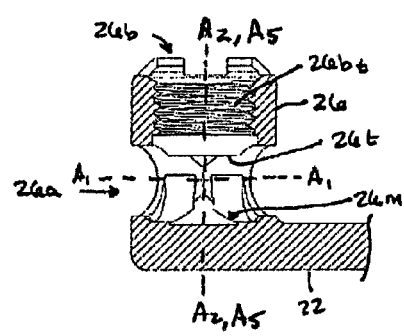
FIG. 1E is a side cross-sectional view of a female member of the spinal cross connector of FIG. 1A.

The housing of the female member 26 can have any shape and size, but in the illustrated embodiment, as best shown in FIG. 1E, the housing has a generally cylindrical configuration with first and second openings 26a, 26b formed therein. The first opening 26a can be configured to receive the male member 36, and the second opening 26b can be configured to receive a fastening element 40 for locking the male member 36 in a fixed position relative to the female member 26. While the openings 26a, 26b can be positioned at various locations relative to one another, in an exemplary embodiment the first opening 26a extends laterally through the housing and the second opening 26b extends vertically through the housing and is in communication with the first opening 26a. As a result, the first opening 26a has an axis $A_1$ that is substantially perpendicular to an axis $A_2$ of the second opening 26b (i.e., the longitudinal axis $A_5$ of the female member 26).

The shape of the first opening 26a in the female member 26 can also vary, but in an exemplary embodiment the first opening 26a in the female member 26 is configured to allow the male member 36 to have at least three degrees of freedom relative to female member 26 prior to locking the male member 36 in a fixed position. While the particular type of movement can vary, in the illustrated embodiment, best shown in FIGS. 1D and 1F, the first opening 26a is configured such that the male member 36 is adjustably slidable within the female member 26 along a longitudinal axis $A_3$ of the male member 36, i.e., the cross connector 10 is telescoping; the male member 36 is rotatable within the female member 26 about the longitudinal axis $A_3$ of the male member 36; and the male member 36 is pivotable or rotatable about a longitudinal axis $A_4$ of the female member 26 such that the longitudinal axis $A_3$ of the male member 36 can be angularly oriented relative to a longitudinal axis $A_4$ of the elongate shaft 22 of the first connector element 20.

Figure 1F:
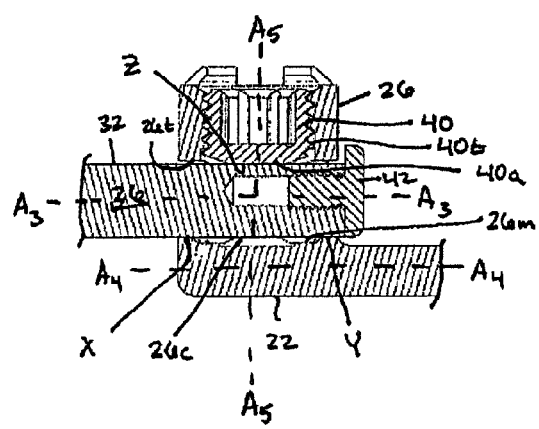
FIG. 1F is a side cross-sectional view of the central portion of the spinal cross connector of FIG. 1A.

The first movement, i.e., sliding movement, is indicated by the arrow labeled S in FIG. 1C. This movement can be achieved by forming the first opening 26a such that it has a size that is sufficient to allow free translation of the male member 36 along the longitudinal axis $A_3$ of the male member 36, i.e., along the axis of the elongate shaft 32. The second movement, i.e., rotational movement about the axis $A_3$ of the male member 36, is indicated by the arrow labeled R in FIG. 1C. This movement is achieved due to the cylindrical shape of the male member 36 as well as the generally cylindrical shape of the first opening 26a formed in the female member 26, as shown in FIGS. 1E and 1F. The third movement, i.e., pivotal or rotational movement about the axis $A_5$ of the female member 26, is indicated by the arrow labeled P in FIG. 1D. This movement can be formed by varying a width of the first opening 26a in the female member 26. As best shown in FIG. 1D, the first opening 26a can include opposed first and second portions $26a_1$, $26a_2$ that increase in width $wo_1$, $wo_2$ from a substantial mid-portion $26a_m$ of the opening 26a toward the opposed ends $26e_1$, $26e_2$ of the opening 26a. This can be achieved by forming a transverse slot through the female member 26 using a cutting tool, and then pivoting the cutting tool about the longitudinal axis $A_5$ of the female member 26. As a result, the male member 36 can pivot or rotate about the longitudinal axis $A_5$ (shown in FIG. 1D as point $A_5$) of the female member 26, i.e., move from side-to-side such that the longitudinal axis $A_3$ of the male member 36 can be angularly oriented relative to a longitudinal axis $A_4$ of the elongate shaft 22 of the first connector element 20. This pivotal or rotational movement is indicated by the arrows labeled R in FIG. 1D. The extent of the such movement can depend on the angle α of the sidewalls of each portion $26a_1$, $26a_2$, but in an exemplary embodiment the first opening 26a is configured to allow the male member 36 to move about 20° in each direction.

The first opening 26a in the female member 26 can also optionally be configured to limit pivotable or rotational movement of the male member 36 about the longitudinal axis $A_5$ of the female member 26 to a single plane. For example, as shown in FIGS. 1E and 1F, the first opening 26a can include opposed top and bottom surfaces 26t, 26m that are substantially planar to prevent the male member 36 from moving up and down. As a result, the male member 36 can only pivot or rotate in a single plane about the longitudinal axis $A_5$ of the female member 26. This will maintain the elongate shaft 22, 32 of the first and second connector elements 20, 30 in a parallel orientation relative to one another. The first opening 26a in the female member 26 can also include other features to facilitate positioning of the male member 36 relative to the female member 26, as will be discussed in more detail below.

The shape of the second opening 26b in the female member 26 can also vary, but as indicated above the second opening 26b is preferably configured to receive a fastening element 40 for locking the male member 36 within the female member 26. In the illustrated embodiment, as best shown in FIGS. 1E and 1F, the second opening 26b has a generally cylindrical shape for receiving a generally cylindrical fastening element. The illustrated fastening element 40 is in the form of a set screw having threads 40t formed thereon that are adapted to mate with corresponding threads 26b, formed within the second opening 26b. Other mating techniques known in the art, such as a twist-lock, interference fit, etc., can alternatively be used instead of threads. When the fastening element 40 is disposed within the second opening 26b, the leading end 40a of the fastening element 40 will contact and abut against the male member 36, and the opposed surface of the male member 36 will rest against a bottom surface 26m of the first opening 26a in the female member 26. The male member 36 will thus be in direct contact with and engaged between the fastening element 40 and the female member 26, and will thereby be locked in a fixed position and prevented from moving relative to the female member 26. As further shown in FIG. 1F, the bottom surface 26m of the first opening 26a in the female member 26 can include a cut-out 26c formed therein such that there are two distinct points of contact, labeled as x and y, between the female member 26 and the male member 36. The cut-out 26c can have various shapes and sizes, but in one embodiment the cut-out 26c can have a generally circular shape, as best shown in FIGS. 1B and 1F, such that the bottom surface 26m of the first opening 26a will include opposed protrusions or raised surface features that the male member 36 will rest against. When the cross connector 10 is fully assembled and the male member 36 is locked within the female member 26, the male member 36 will thus have three distinct points of contact, one (labeled as z in FIG. 1F) with the fastening element 40 and the other two (x, y) with the female male 26. Such a configuration is particularly advantageous as it can help prevent undesired angulation of the male member 36 when the male member 36 is locked within the female member 26, thereby maintaining the elongate shafts 22, 32 of the first and second connector elements 20, 30 in substantially parallel planes of motion.

The male and female members 26, 36 can also include a variety of other features. For example, as shown in FIGS. 1A-1D and 1F, the male member 36 can include a retaining element 42 formed thereon or coupled thereto for preventing removal of the male member 36 from the first opening 26a in the female member 26. In the illustrated embodiment, best shown in FIG. 1B, the retaining element 42 is in the form of a threaded shaft 42a having an enlarged head 42b formed thereon. The shaft 42a is configured to be threadably disposed within a threaded bore 36t (FIG. 1B) formed in the terminal end of the male member 36, and the enlarged head 42b has a diameter that is greater than a width of the first opening 26a in the female member 26 to prevent passage of the head 42b therethrough, and to thus retain the male member 36 within the female member 26. Various other exemplary retaining elements will be discussed in more detail below with respect to FIGS. 13A-15B. The female member 26 can similarly include a retaining element formed thereon or coupled thereto for preventing removal of the fastening element 40 from the second opening 26b in the female member 26. In the illustrated embodiment, the female member 26 includes several tabs 26f (FIG. 1A) disposed around a perimeter of the top of the female member 26. The tabs 26f can be swaged or deformed inward during manufacturing to engage the fastening element 40, e.g., the threads on the fastening element 40, thereby allowing rotation of the fastening element 40 while prevent removal of the fastening element 40 from the female member 26.

The cross connector 10 can also include other features. For example, as will be discussed in more detail with respect to the embodiment shown in FIG. 7A, the cross connector 10 can include one or more bend zones formed therein and configured to allow the cross connector 10 to be deformed into a desired configuration. The bend zones can be formed at any location on the cross connector 10, but in certain exemplary embodiments one or more bend zones are formed in the elongate shaft 22, 32 of the first and/or second connector elements 20, 30. Other features of the cross connector 10 can include, for example, grasping notches to facilitate grasping and manipulation of the device 10. FIG. 1A illustrates first and second grasping notches 24n, 34n formed in opposed sides of each connector head 24, 34. A tool, such as a grasper, can engage the grasping notches 24n, 34n to manipulate the connector heads 24, 34 as desired. FIG. 1A also illustrates several notches 26n formed around a perimeter of the female member 26. These notches 26n can likewise be engaged using a grasper or other tool to facilitate manipulation of the female member 26. The notches 26n can also be used to attach an instrument to apply a counter torque to the central portion of the cross connector during final tightening of the fastening element. This prevents any force from being transferred to the spinal fixation elements while applying the final tightening torque to the fastening element. In an exemplary embodiment, one or more of the notches 24n, 34n, 26n can have a dovetail configuration to allow a tool having a complementary dovetail formed thereon to extend into and engage the notch 24n, 34n, 26n. A person skilled in the art will appreciate that various other techniques can be used to facilitate manipulation of the cross connector 10.

Other exemplary features of the cross connector 10 include, for example, a snap-fit mechanism that provides audible and/or tactile feedback when a spinal fixation element is positioned within a recess 25, 35 in the cross connector 10. FIGS. 1A-1C illustrate one exemplary snap-fit mechanism that is in the form of a deflectable member 46a, 46b formed adjacent to the recess 25, 35 in each connector head 24, 34. The deflectable members 46a, 46b can be formed, for example, by cutting a slit or groove in the bottom surface 24b, 34b of the connector head 24, 34. In use, as a spinal fixation element is received within the recess 25, 35, the deflectable member 46a, 46b will deflect outward, thereby increasing a size of the recess 25, 35. Once the spinal fixation element is fully received in the recess 25, 35, the deflectable member 46a, 46b will return to its initial position, snapping around the spinal fixation element to provide a tactile and/or audible signal that the spinal fixation element is fully loaded within the recess 25, 35.

Figure 1G:
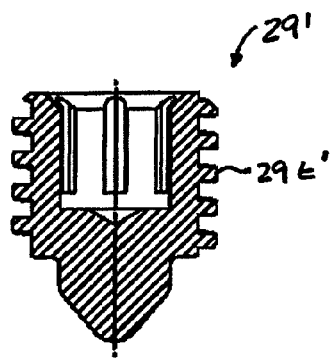
FIG. 1G is a cross-sectional view of one embodiment of a locking mechanism for use with a spinal cross connector.
Figure 1H:
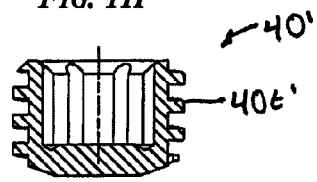
FIG. 1H is a cross-sectional view of one embodiment of a fastening element for use with a spinal cross connector.
Figure 1I:
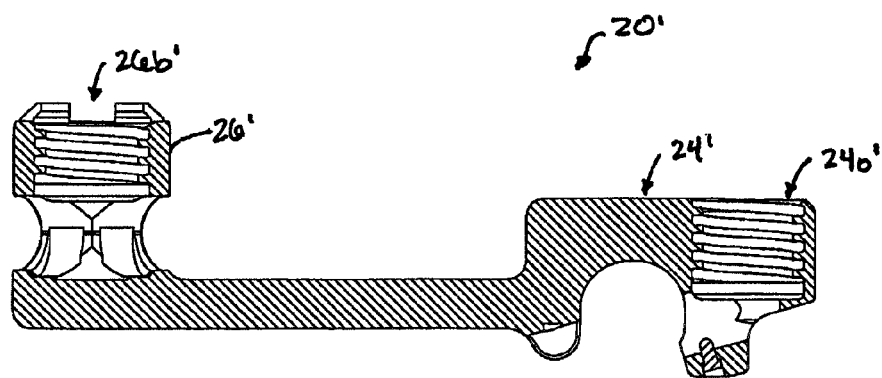
FIG. 1I is a cross-sectional view of an alternative embodiment of a portion of a spinal cross connector having openings configured to receive the locking mechanism and fastening element of FIGS. 1G and 1H.

FIGS. 1G-1I illustrate another embodiment of a technique for mating a fastening element and/or locking mechanism to a cross connector. In general, FIG. 1G illustrates a locking mechanism 29' that is similar to the locking mechanisms 29, 39 shown in FIGS. 1A-1B. However, in this embodiment the locking mechanism 29' has square threads 29t' formed thereon. FIG. 1H likewise illustrates a fastening element 40' that is similar to the fastening element 40' shown in FIGS. 1A and 1B. However, in this embodiment the fastening element 40' includes square threads 40t' formed thereon. FIG. 1I illustrates another embodiment of the first connector element 20' having square threads formed in the opening 24o' in the connector head 24' for mating with the corresponding square threads 29t' formed on the locking mechanism 29', and having square threads formed in the opening 26b' of the female member 26' for mating with the square threads 40t' formed on the fastening element 40'. The use of square threads on the various fastening elements and locking mechanisms disclosed herein is particularly advantageous in that the square threads provide an evenly distributed axial compression load to the male member or the engagement mechanism, thereby preventing slippage.

Figure 2C:
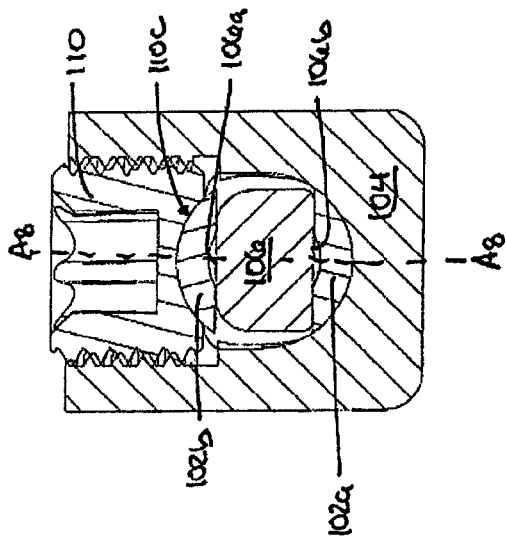
FIG. 2C is another side cross-sectional view of a central portion of the spinal cross connector of FIG. 2A.
Figure 2B:
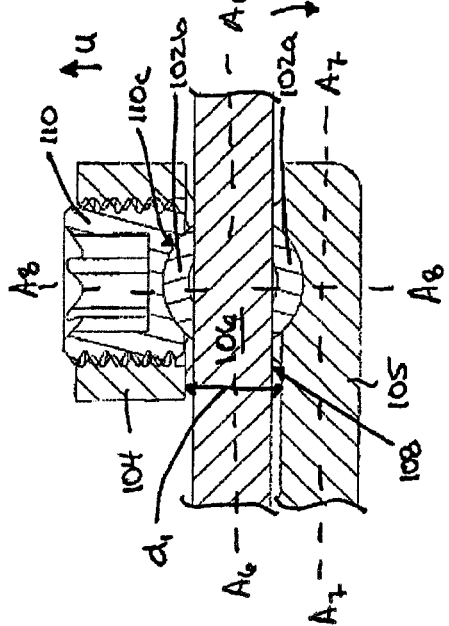
FIG. 2B is a side cross-sectional view of a central portion of the spinal cross connector of FIG. 2A.

FIGS. 2A-2D illustrate another embodiment of a technique for adjusting a central portion of a cross connector, and in particular for allowing movement between male and female members of the cross connector prior to locking the male member within the female member. In this embodiment, the cross connector 100 includes an insert 102 that is movably disposed within a female member 104 and that seats the male member 106 to allow the male member 106 to be selectively positioned relative to the female member 102. In particular, the insert 102 is formed from two components, a first insert 102a and a second insert 102b. Each insert 102a, 102b has a generally hemi-spherical shape with a convex surface $102a_1$, $102b_1$ and an opposed planar surface $102a_2$, $102b_2$. The female member 104 includes first and second openings 108, 110 extending therethrough that are similar to the first and second openings 26a, 26b previously discussed with respect to the embodiment shown in FIGS. 1A-1F. However, in this embodiment, the first opening 108 includes a substantially concave cavity 108a formed in a bottom surface thereof that is configured to movably seat one of the inserts, i.e., the first insert 192a, and the fastening element 110 that is received within the second opening 110 includes a concave cavity 110c formed in a distal end thereof for movably seating the second insert 102b, as shown in FIGS. 2B and 2C. As a result, the male member 106 of the second connector element can be disposed through the first opening 108 in the female member 104 such that the male member 106 is positioned between and surrounded by the first and second inserts 102a, 102b. In an exemplary embodiment, as shown in FIG. 2C, the male member 106 has a substantially rectangular shape with opposed planar surfaces 106a, 106b to facilitate positioning of the male member 106 between the planar surfaces $102a_2$, $102b_2$ of the first and second inserts 102a, 102b. The male member 106, as well as the planar surfaces $102a_2$, $102b_2$ on the first and second inserts 102a, 102b, can have a variety of other shapes and sizes to facilitate positioning between the three components.

Figure 2D:
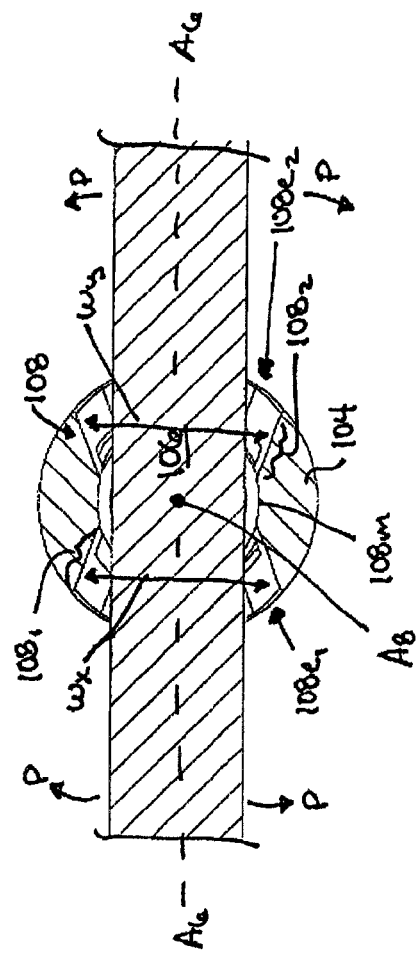
FIG. 2D is a top cross-sectional view of a central portion of the spinal cross connector of FIG. 2A.

In use, the male member 106 is adjustably slidable within the female member 104 along a longitudinal axis $A_6$ of the male member 106, i.e., the cross connector is telescoping; the male member 106 is rotatable within the female member 104 about the longitudinal axis $A_6$ of the male member 106; and the male member 106 is polyaxially movable about the longitudinal axis $A_g$ of the female member 104 such that the longitudinal axis $A_6$ of the male member 106 can be angularly oriented relative to a longitudinal axis $A_7$ of the elongate shaft 105 extending from the female member 104. Translation and rotation about the axis $A_6$ of the male member 106 are merely allowed due to the configuration of the male member 106 and the first and second inserts 102a, 102b. The hemi-spherical shape of the first and second inserts 102a, 102b also allows polyaxial movement of the male member 106 about a longitudinal axis $A_g$ of the female member 104 such that a longitudinal axis $A_6$ of the male member 106 can be angularly oriented relative to a longitudinal axis $A_7$ of the elongate shaft 105 that extends from the female member 104. As with the embodiment previously discussed with respect to FIGS. 1A-1F, the direction and amount of movement in each direction of the male member 106 relative to the female member 104 can optionally be limited by the configuration of the first opening 108 in the female member 104. For example, as shown in FIG. 2D, the first opening 108 can include opposed first and second portions $108_1$, $108_2$ that increase in width $w_x$, $w_y$ from a substantial mid-point 108m of the opening 108 toward the opposed ends $108e_1$, $108e_2$ of the opening 108. As a result, the male member 106 can pivot or rotate about the longitudinal axis $A_g$ (shown as point $A_g$ in FIG. 2D) of the female member 104, i.e., move from side-to-side in a plane that extends horizontally through the longitudinal axis $A_g$ of the female member 104. This movement is indicated by the arrows labeled P in FIG. 2D. As with the embodiment shown in FIGS. 1A-1F, the extent of the pivotal or rotational movement about axis $A_g$ can depend on the angle of the sidewalls of each portion $108_1$, $108_2$, but in an exemplary embodiment the first opening 108 is configured to allow the male member 106 to move side-to-side about 20° in each direction.

The first opening 108 in the female member 104 can also optionally be configured to allow some polyaxial movement of the male member 106 about the longitudinal axis $A_8$ of the female member 104 such that the male member 106 can extend in a plane that intersects a plane containing the elongate shaft 105 extending from the female member 104. This movement is hereafter referred to as angulation of the male member 106 about the longitudinal axis of the female member 104. For example, as shown in FIG. 2B, the distance $d_1$ between the top and bottom surfaces of the first opening 108 can limit up-down movement of the male member 106, which is indicated by the arrows labeled U and D in FIG. 2B. In an exemplary embodiment, the first opening 108 is configured to allow the male member 106 to move up and down about 4° in each direction. The first opening 108 can also limit rotation of the male member 106 about its longitudinal axis $A_6$. This can be achieved by forming a square or rectangular shape within the first opening 108 that complements the square or rectangular configuration of the male member 106. Thus, while the inserts 102a, 102b allow some rotation of the male member 106 about its longitudinal axis $A_6$, the square or rectangular opening 108 extending transversely through the female member 104, as well as the square or rectangular shape of the male member 106, will limit the amount of rotation. In an exemplary embodiment, the male member 106 can rotate about 14° in each direction about its longitudinal axis $A_6$. A person skilled in the art will appreciate that the range of motion as well as the direction of motion can vary depending on the particular configuration of the insert 102, the male member 106, and the opening(s) 108, 110 in the female member 104.

In use, as indicated above, the male member 106 is positioned between the first and second inserts 102a, 102b such that that inserts 102a, 102b allow polyaxial movement of the male member 106 relative to the female member 104. Once the male member 106 is positioned in a desired angular orientation, the fastening element 110 can be tightened to lock the male member 106 in a fixed position relative to the female member 104. As the fastening element 110 is tightened, for example by threading the fastening element 110 into the second opening 110 in the female member 104, the second insert 102b will be received within the concave cavity 110c formed in the distal-facing surface of the fastening element 110, and the fastening element 110 will apply a force to the second insert 102b which in turn will apply a force to the male member 106 and to the first insert 102a to thereby lock the male member 106 in a fixed position relative to the female member 104 such that movement between the two components is prevented.

The male and female members 104, 106 can also include a variety of other features. For example, as previously discussed with respect to FIGS. 1A-1D and 1F, the male member can include a retaining element formed thereon or coupled therefore for preventing removal of the male member from the first opening in the female member. Various other exemplary retaining elements will be discussed in more detail below with respect to FIGS. 13A-15B. The female member can similarly include a retaining element formed thereon or coupled thereto, as previously discussed with respect to FIGS. 1A-1F, for preventing removal of the fastening element from the second opening in the female member. This will also retain and prevent removal of the inserts from the female member, thereby eliminating the need to assembly the device during use.

Figure 3A:
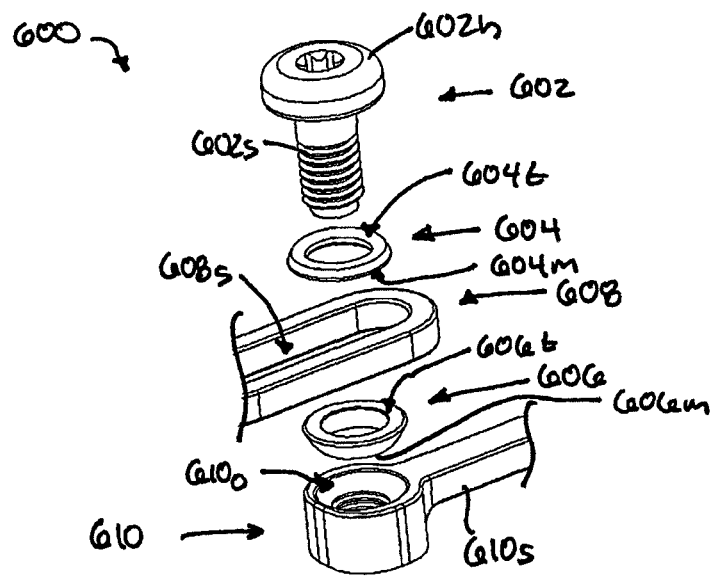
FIG. 3A is an exploded view of another embodiment of a spinal cross connector having an adjustable central portion.

FIGS. 3A-6B illustrate various other techniques for providing an adjustable central portion to allow movement between first and second connector elements of a cross connector prior to locking the central portion. FIGS. 3A and 3B illustrate one embodiment of a central portion 600 that is similar to the embodiment shown in FIGS. 2A-2D, but that utilizes a fastening element 602 that is inserted through first and second inserts 606, 604, and through a male member 608 to mate to a female member 610. In particular, in this embodiment the female member 610 is in the form of a housing formed on the terminal end of an elongate member 610s and having a single opening 610o extending longitudinally therethrough for receiving the fastening element 602. A proximal portion of the opening 610o can include a concave cavity 610c formed therein and adapted to movably seat one of the inserts, i.e., the first insert 606, as will be discussed below. A distal portion of the opening 610i can include threads 610t formed therein for mating with corresponding threads formed on the fastening element 602. The male member 608 can have an elongate planar configuration with a slot 608s extending longitudinally therethrough for receiving the fastening element 602. While not shown, the slot 608s can extend along the entire length of the male member 608 such that the slot 608s terminates adjacent to the connector head, or it can extend along only a portion of the male member 608 and the remainder of the male member 608 can be in the form of a shaft that mates to the connector head. As indicated above, the central portion 600 further includes first and second inserts 606, 604. In this embodiment, each insert 606, 604 has a generally hemi-spherical configuration, however the top and bottom surfaces 606t, 606m, 604t, 604m of each insert 606, 604 are substantially planar. Thus, only the outer edge of each insert 606, 604 is convex. Each insert 606, 604 also includes a central opening formed therethrough for receiving the fastening element 602. In an exemplary embodiment, the first insert 606 has a width $w_i$ extending between the top and bottom surfaces 606t, 606m that is greater than a width $w_j$ of the second insert 604. This will allow the first insert 606 to be seated within the concave cavity 610c formed in the female member 610, and the second insert 604 to be seated within a concave cavity 602c formed in a distal facing surface of the fastening element 602. The cavity 602c in the fastening element 602, shown in FIG. 3B, can be formed in an enlarged head 602h that is coupled to a threaded shaft 602s of the fastening element 602.

Figure 3B:
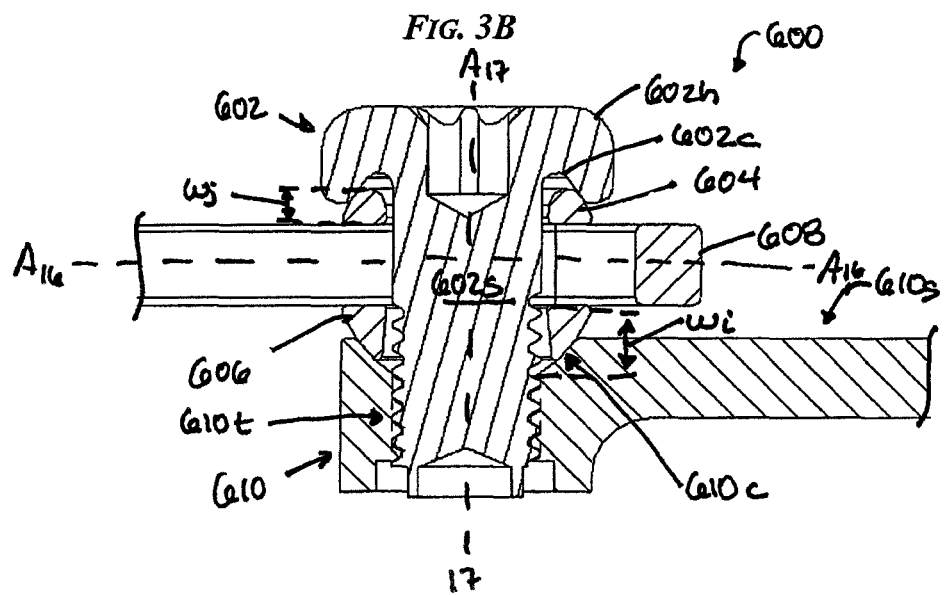
FIG. 3B is a cross-sectional view of the central portion of FIG. 3A shown in the assembled configuration.

When the center portion 600 is fully assembled, as shown in FIG. 3B, the threaded shaft 602s of the fastening element 602 is passed through the second insert 604, the slot 608s in the male member 608, the first insert 606, and into the opening 610o formed in the female member 610. The threads on the threaded shaft 602s of the fastening element 602 can mate with the threads 610t formed in the opening 610o in the female member 610, or various other mating techniques known in the art can be used. Prior to fully tightening the fastening element 602, the male member 608 can translate along its longitudinal axis $A_{16}$ due to the slot 608s extending through the male member 608. The male member 608 can also rotate about its longitudinal axis $A_{16}$ due to the inserts 604, 606. And the male member 608 can polyaxially move or be angularly oriented about an axis $A_{17}$ extending through the opening 610o in the female member 610 and through the fastening element 602 due to the first and second inserts 606, 604. In particular, as with the embodiment previously discussed with respect to FIGS. 2A-2D, the convex outer surfaces of the inserts 606, 604, in combination with the cavity 610c in the opening 610o of the female member 610 and the cavity 602c in the head 602h of the fastening element 602, allow the inserts 606, 604 to polyaxially move relative to the female member 610 and fastening element 602. The various movements can, however, be limited by the particular shape and size of the cavities 610c, 602c in the female member 610 and the fastening element 602. In an exemplary embodiment, pivotal or rotational movement about the longitudinal axis $A_{17}$ of the opening 610a and the fastening element 602 is unlimited (except for limitations due to the configuration of each connector head), while rotation of the male member 608 about its longitudinal axis $A_{16}$ is limited by the cavities 610c, 602c. By way of non-limiting example, rotation of the male member 608 about its axis $A_{16}$ can be limited to about 5° in each direction. Polyaxial movement about axis $A_{17}$ can also be limited by the shape of the cavities 610c, 602c, which will function as a stop against which the male member 608 will abut.

Figure 4A:
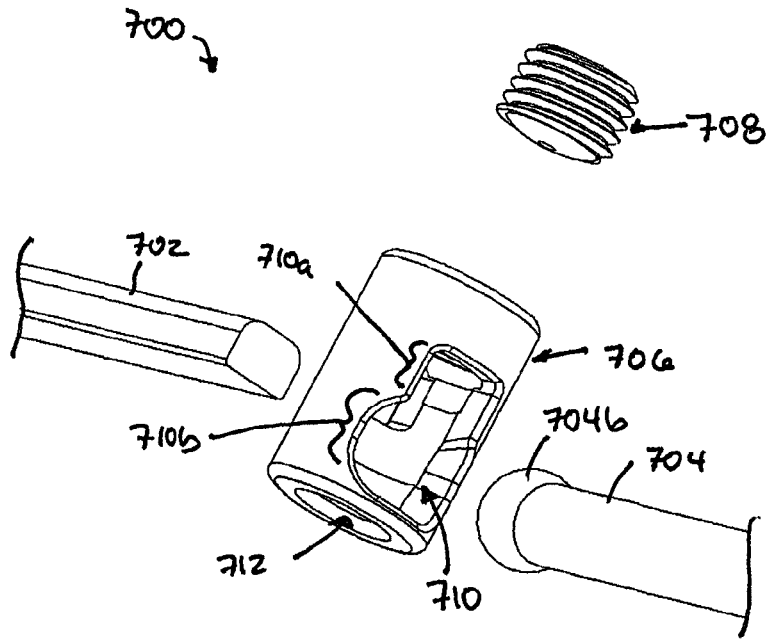
FIG. 4A is an exploded view of another embodiment of a spinal cross connector having an adjustable central portion.
Figure 4B:
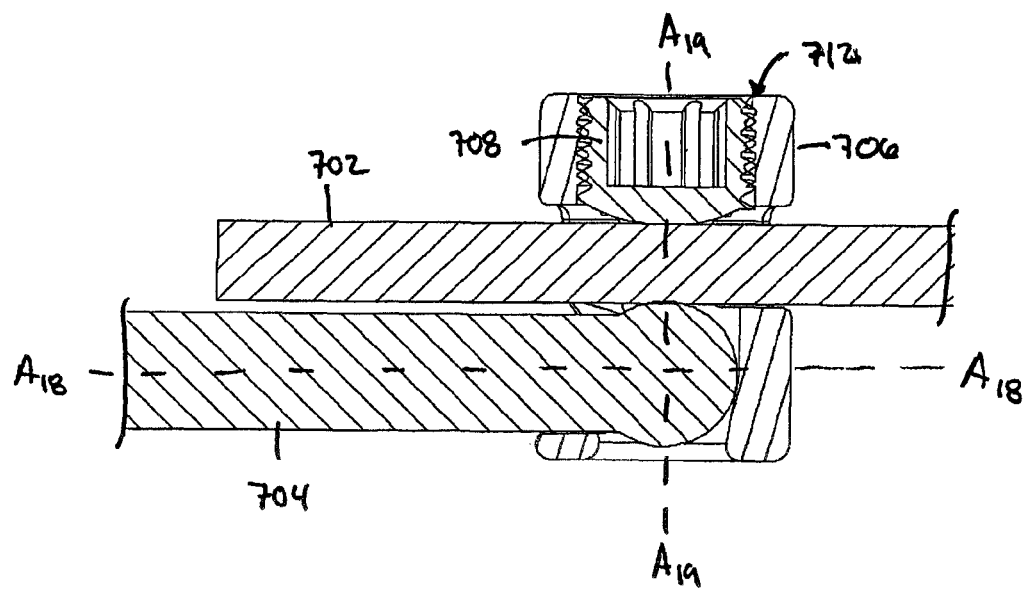
FIG. 4B is a cross-sectional view of the central portion of FIG. 4A shown in the assembled configuration.

In another embodiment, shown in FIGS. 4A-4B, the central portion 700 of the cross connector can include two separate elongate members 702, 704 that mate to a separate female member 706, and that are configured such that the first elongate member 702 can slidably move along its longitudinal axis, the second elongate member 704 can rotate about its longitudinal axis, and the second elongate member 704 is polyaxially movable about a longitudinal axis of the female member 706. The female member 706 can be similar to the housing that forms the female member 26 of FIGS. 1A-1B, and it can include first and second openings 710, 712 extending therethrough. In this embodiment, however, the first opening 710 includes proximal and distal portions 710a, 710b. The proximal portion 710a is shaped to receive one of the elongate members, e.g., member 702, and the distal portion 710b is shaped to receive the other elongate member, e.g., member 704. While the particular shape of each portion 710a, 710b can vary depending on the shape of each shaft 702, 704, in an exemplary embodiment, as shown, the proximal portion 710a has a rectangular shape that complements the rectangular shape of the first elongate member 702, and the distal portion 710b has a partially spherical or concave cavity formed therein for seating a spherical member 704b formed on the distal end of the second elongate member 704. In an exemplary embodiment, the proximal portion 710a extends entirely through the female member 706, while the distal portion 710b is merely an opening formed in one side of the female member 706. The cavity in the distal portion 710b can also be tapered toward the distal end of the female member 706, i.e., the width of the cavity can decrease from a proximal end to a distal end, to form a wedge-shaped inner sidewall that will assist in engaging the spherical member 704b on the second elongate member 704.

In use, the first and second elongate members 702, 704 will be engaged between the fastening element 708 and the distal end of the female member 706. Prior to locking the fastening element 708, the elongate members 702, 704 can be angularly oriented relative to one another. In particular, the proximal portion 710a of the first opening 710 can allow translation of the first elongate member 702, while preventing rotation movement of the first elongate member 702 about its axis and about the axis $A_{19}$ of the female member 706 due to the rectangular cross-sectional shape of the first elongate member 702 and the proximal portion 710a of the first opening 710. The distal portion 710b of the first opening 710, on the other hand, can prevent translation while allowing full rotation of the second elongate member 704 about its axis $A_{18}$, as well as some polyaxial movement of the second elongate member 704 about the axis $A_{19}$ of the female member 706. The range of polyaxial movement, which can include side-to-side, up-down motion, and combinations thereof, can be limited by the size and shape of the distal portion 710b of the opening 710, as with the previous embodiments discussed herein. For example, the bottom surface of the distal portion 710b of the opening 710, in combination with the location of the first elongate member 702 extending through the proximal portion 710a of the opening, can limit up-down movement, i.e., movement in a plane that extends through the axis $A_{19}$ of the female member 706. In an exemplary embodiment, up-down movement is limited to about 5° in each direction. The distal portion 710b of the opening 710 can, however, allow more significant side-to-side movement, i.e., pivotal or rotational movement about the longitudinal axis $A_{19}$ of the female member 706. This can be achieved by forming lateral portions with increasing widths on each side of the distal portion 710b of the opening 710, as previously explained with respect to FIG. 2D.

Figure 5A:
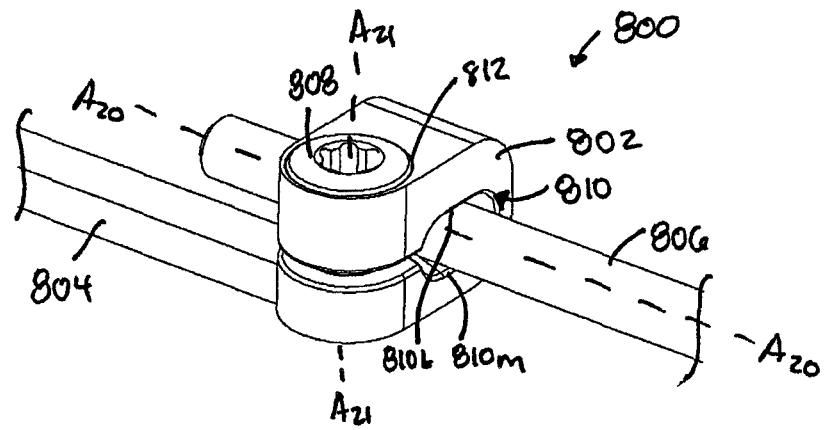
FIG. 5A is a perspective view of yet another embodiment of an adjustable central portion of a spinal cross connector.
Figure 5B:
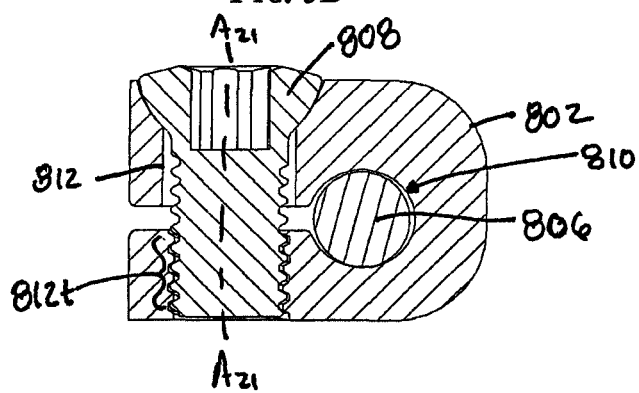
FIG. 5B is a side cross-sectional view of the central portion shown in FIG. 5A.
Figure 5C:
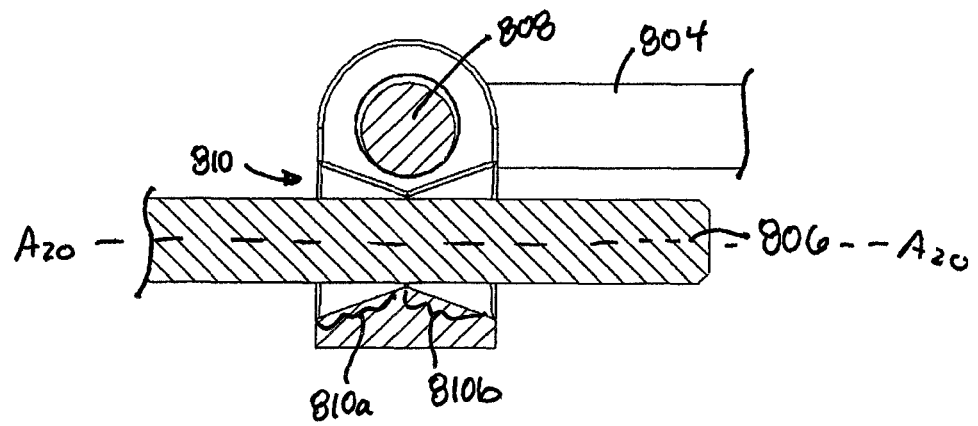
FIG. 5C is a top cross-sectional view of the central portion shown in FIG. 5A.

In yet another embodiment, shown in FIGS. 5A-5B, the central portion 800 can include a first elongate member 804 having a female member in the form of a clamp 802 formed on a terminal end thereof, and a second elongate member 806, i.e., a male member, that is configured to be movably received within the clamp 802. The clamp 802 can have a generally c-shaped configuration that defines a first opening 810 extending laterally therethrough and configured to receive the second elongate member 806. A second opening 812 can extend longitudinally through the opposed ends of the c-shaped clamp 802 and it can be configured to receive a fastening element 808 for closing the clamp 802 and locking the second elongate member 806 in a fixed position relative to the first elongate member 804. In an exemplary embodiment, as shown, the shape of the first opening 810 can be configured to allow the second elongate member 806 to translate or slide along its longitudinal axis $A_{20}$, rotate about its longitudinal axis $A_{20}$, and pivot or rotate about a longitudinal axis $A_{21}$ extending through the second opening 812 in the clamp 802. In particular, the second elongate member 806 can have a substantially cylindrical shape to allow for full rotation and translation about its axis $A_{20}$. Pivotal or rotational movement about axis $A_{21}$ can be achieved by increasing a width of the first opening 810 from a mid-portion thereof. This is illustrated in FIG. 5C, which shows first and second portions 810a, 810b that increase in width from a mid-portion of the first opening 810. Such a configuration was previously described with respect to FIG. 2D. In an exemplary embodiment, pivotal or rotational movement of the second elongate member 806 about the longitudinal axis $A_{21}$ of the second opening 812 in the clamp 802 can be limited to about 20° in each direction. Up-down movement, i.e., movement in a plane that extends through axis $A_{21}$, can be limited by substantially planar top and bottom surfaces 810t, 810m of the first opening 810, as shown in FIG. 5A. As a result, the elongate member 806 can be limited to movement about axis $A_{21}$ in a single plane. In use, once the second elongate member 806 is positioned as desired relative to the first elongate member 804, the fastening element 808 can be inserted through the second opening 812 in the clamp 802 to pull the ends of the clamp 802 together, and thereby close the first opening 810, i.e., decrease a width of the first opening 810 extending between the top and bottom surfaces 810t, 810m. This will engage the second elongate member 806 and prevent it from moving relative to the first elongate member 804. The fastening element 808 can be mated to the clamp 802 using a variety of techniques. In the illustrated embodiment, the fastening element 808 is threaded to mate with a threaded portion 812t formed in the second opening 812, as shown in FIG. 5B.

Figure 6A:
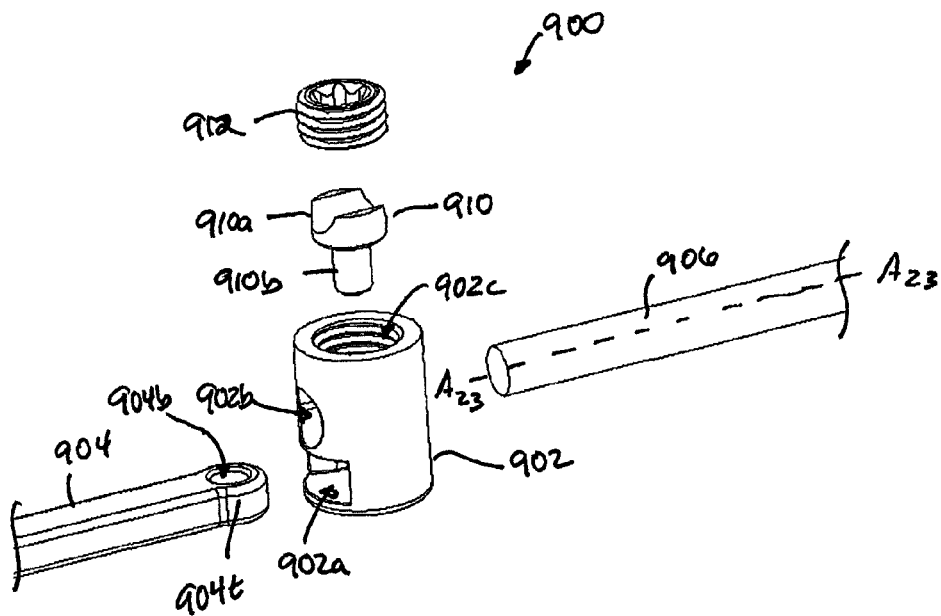
FIG. 6A is an exploded view of a cross connector having an adjustable central portion according to yet another embodiment.
Figure 6B:
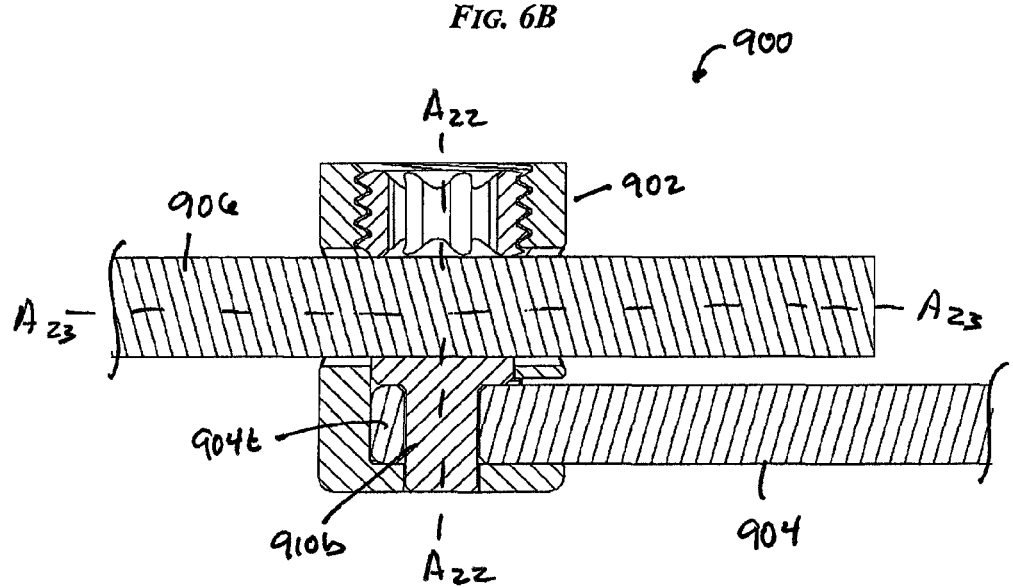
FIG. 6B is a cross-sectional view of the central portion of FIG. 6A shown in the assembled configuration.

FIGS. 6A-6B illustrate another embodiment of a technique for providing an adjustable cross connector. In this embodiment, the central portion 900 includes a female member 902, in the form of a housing, that receives separate elongate members 904, 906. An insert 910 is disposable within the female member 902 and it is positioned between the elongate members 904, 906 to allow movement therebetween. A fastening element 912 is also received within the female member 902 to lock the first and second elongate members 904, 906 within the female member 902. The female member 902 can include three openings formed therein for receiving the first and second elongate members 904, 906, the insert 910, and the fastening element 912. In particular, the first opening 902a can extend laterally through a distal portion of the female member 902 for receiving the first elongate member 904. In an exemplary embodiment, as shown, the first opening 902a is formed in only one sidewall of the female member 902 and extends into a cavity having a shape that complements a shape of a terminal end of the first elongate member 904. In the illustrated embodiment, the first elongate member 904 includes a substantially circular member 904t formed on the terminal end thereof and thus the first opening 902a can include a circular cavity formed therein. The width of the first opening 902a is also preferably greater than a width of the circular member 904t. This configuration will allow the first elongate member 904 to pivot or rotate about a longitudinal axis $A_{22}$ of the female member 902 when disposed therein. As further shown in FIGS. 6A and 6B, the circular member 904t on the terminal end of the first elongate member 904 can also include a bore 904b formed therethrough for receiving a portion of the insert 910. In particular, the insert 910 can include a proximal head 910a and a distal post 910b extending distally from the head 910a. The post 910b can extend through the bore 940b in the circular member 904t of the first elongate member 904 when the device is assembled. In an exemplary embodiment, the post 910b and the bore 904b are cylindrical to allow the insert 910, and thus the first elongate member 904, to pivot or rotate about the longitudinal axis $A_{22}$ of the central portion 900. The head 910a of the insert 910 can include a concave cavity extending longitudinally therethrough for seating the second elongate member 906, which in an exemplary embodiment has a generally cylindrical configuration. Such a configuration will allow the second elongate member 906 to translate and rotate about its longitudinal axis $A_{23}$. As indicated above, the central portion 900 can also include a fastening element 912 that locks the first and second elongate members 904, 906 in a fixed position relative to one another, and relative to the female member 902. In the illustrated embodiment, the fastening element 912 is in the form of a threaded set screw that mates with threads formed in the third opening 902c extending through the female member 902. When fully threaded into the third opening 902c, the fastening element 912 will apply a force to the second elongate member 906, which in turn will apply a force to the insert 910 which bears against the first elongate member 904 to thereby lock the components within the female member 902.

FIGS. 7A-8B illustrate other exemplary embodiments of spinal cross connectors. In these embodiments, the cross connectors 300, 400 have a fixed length, rather than a telescoping configuration. In each embodiment, the cross connector 300, 400 generally includes an elongate body 302, 402 having opposed top and bottom surfaces 302a, 302b, 402a, 402b, and opposed first and second ends 302c, 302d, 402c, 402d. First and second recesses 304, 306, 404, 406 are formed in the bottom surface 302b, 402b of each body 302, 402 for receiving first and second spinal fixation elements, and first and second openings 308, 310, 408, 410 are formed in the top surface 302a, 402a for receiving first and second locking mechanisms 320, 322, 420, 422 for locking spinal fixation elements within the first and second recesses 304, 306, 404, 406. Many of the features shown in FIGS. 7A-8B are similar to those previously described, and thus will not be discussed in further detail. For example, the locking mechanisms 320, 322, 420, 422 can be similar to the locking mechanisms 29, 39 shown and described with respect to FIGS. 1A and 1B. The cross connectors 300, 400 can also include engagement members or shoes 312, 314, 412, 414 similar to those previously described with respect to FIGS. 1A and 1B, and as will be discussed in more detail below with respect to FIGS. 9A-12C.

While the cross connectors shown in FIGS. 7A-8B are similar, one difference is the location of the openings 308, 310, 408, 410 that receive the locking mechanisms 320, 322, 420, 422 relative to the recesses 304, 306, 404, 406 that receive the spinal fixation elements. In the embodiment shown in FIGS. 7A-7B, the recesses 304, 306 in the elongate body 302 are positioned between or laterally inward of the openings 308, 310 that receive the locking mechanisms 320, 322 such that the locking mechanisms 320, 322 will be positioned laterally outward from the recesses 304, 306. Conversely, in the embodiment shown in FIGS. 8A-8B the recesses 404, 406 in the elongate body 402 that receive the spinal fixation elements are positioned laterally outward of the openings 408, 410 that receive the locking mechanisms 420, 422 such that the locking mechanisms 420, 422 will be positioned medially inward from the recesses 404, 406. These two orientations allow the user to select the appropriate cross connector based on the implant location of the spinal fixation elements.

Figure 7A:
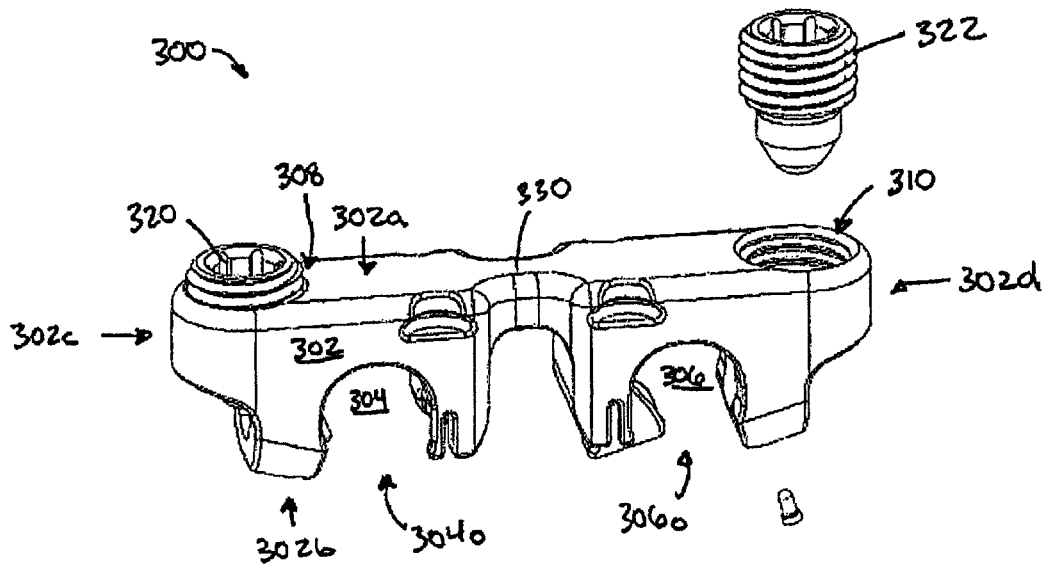
FIG. 7A is a perspective, partially exploded view of yet another embodiment of a spinal cross connector having locking mechanisms located laterally outward from first and second recesses formed in the cross connector and configured to receive first and second spinal fixation elements.
Figure 7B:
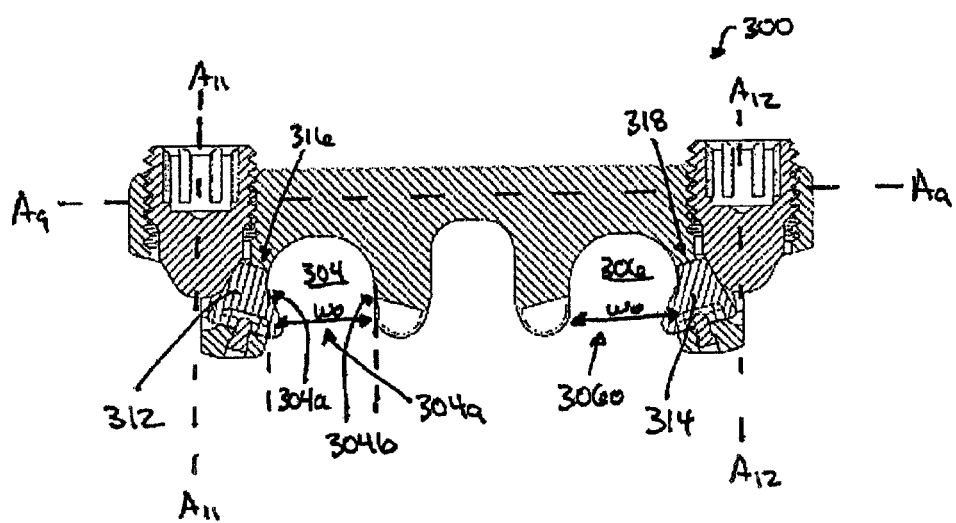
FIG. 7B is a side cross-sectional view of the spinal cross connector of FIG. 7A.
Figure 8A:
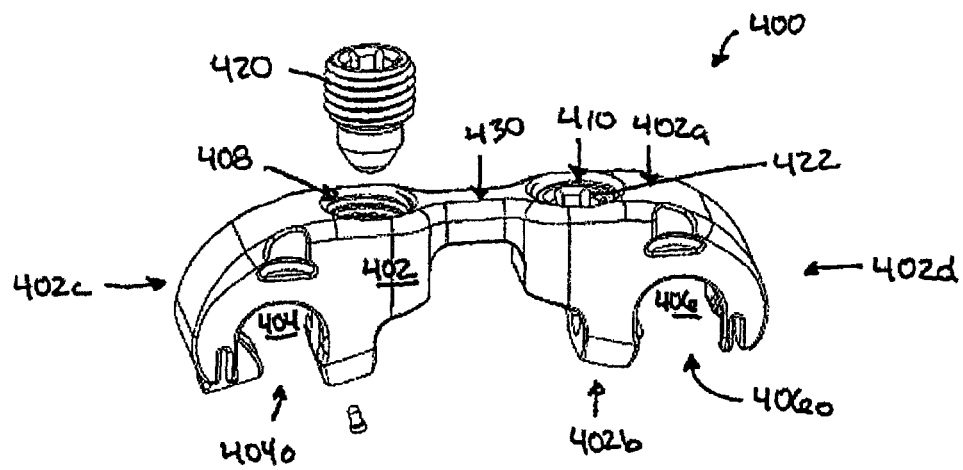
FIG. 8A is a perspective, partially exploded view of yet another embodiment of a spinal cross connector having locking mechanisms located laterally inward from first and second recesses formed in the cross connector and configured to receive first and second spinal fixation elements.
Figure 8B:
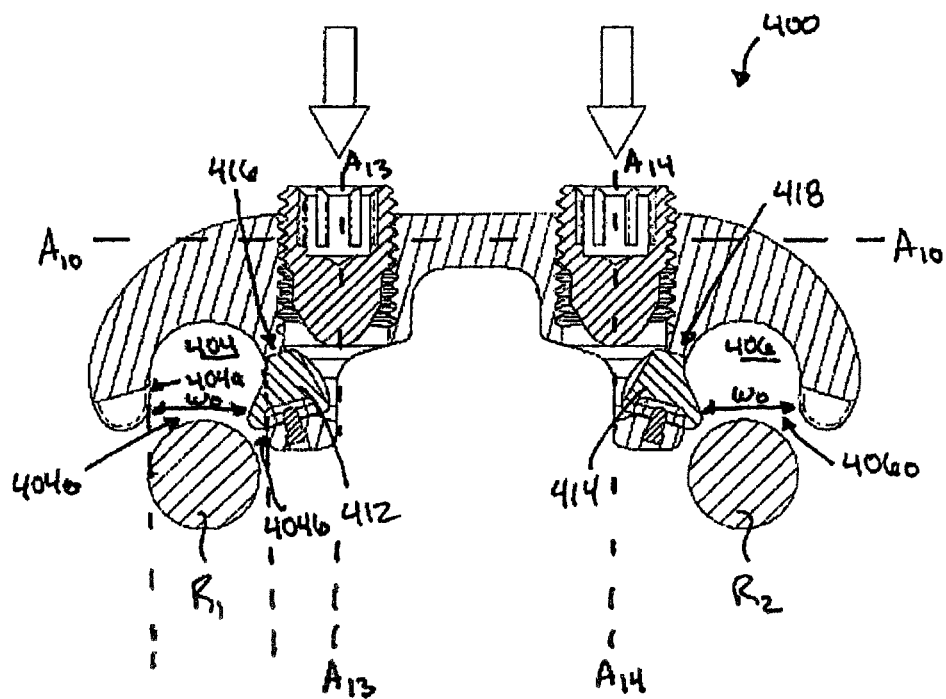
FIG. 8B is a side cross-sectional view of the spinal cross connector of FIG. 8A, showing the spinal cross connector about to be loaded onto first and second spinal fixation elements.

As further shown in FIGS. 7A-8B, the recesses 304, 306, 404, 406 can being oriented to enable the cross connectors 300, 400 to be simultaneously top-loaded onto first and second spinal fixation elements. In particular, each recess 304, 306, 404, 406 can include opposed sidewalls that are substantially parallel to one another, and that are substantially perpendicular to a longitudinal axis $A_9$, $A_{10}$ of the elongate body 302, 402. This is illustrated in FIGS. 7B and 7C, which show sidewalls 304a, 304b in recess 304 and sidewalls 404a, 404b in recess 404 having parallel orientations. As a result, each recess 304, 306, 404, 406 will have a distal-facing opening 304o, 306o, 404o, 406o that is oriented in the same direction to allow two substantially parallel spinal fixation elements, such as spinal rods, to be simultaneously received therein. FIG. 8B illustrates the cross connector 400 being advanced toward two substantially parallel spinal rods $R_1$, $R_2$. Since the recesses 304, 306, 404, 406 are not angled relative to one another, the parallel configuration eliminates the need to sequentially load a spinal fixation element into each recess 304, 306, 404, 406. The size of the distal-facing opening 304o, 306o, 404o, 406o in each recess 304, 306, 404, 406 can also facilitate simultaneous loading. In an exemplary embodiment, the distal-facing opening 304o, 306o, 404o, 406o in each recess 304, 306, 404, 406 has a width $w_o$ that is greater than a maximum width or diameter of a spinal fixation element being received therein.

In addition to having substantially parallel recesses 304, 306, 404, 406 that are substantially perpendicular to a longitudinal axis $A_9$, $A_{10}$ of the elongate body 302, 402, the first and second openings 308, 310, 408, 410 formed in the top surface 302a, 402a of the elongate body 302, 402 can also be configured to receive the locking mechanisms 320, 322, 420, 422 in a parallel orientation. In particular, the openings 308, 310, 408, 410 can have longitudinal axes $A_{11}$, $A_{12}$, $A_{13}$, $A_{14}$ that are substantially parallel to one another, substantially parallel to the sidewalls of the recesses 304, 306, 404, 406, and substantially perpendicular to the longitudinal axis $A_9$, $A_{10}$ of the elongate body 302, 304, as shown. Thus, the openings 308, 310, 408, 410 and the recesses 304, 306, 404, 406 can be oriented in the same direction, i.e., substantially parallel to an axis of loading the cross connector 300, 400 onto first and second spinal fixation elements. Such a configuration will facilitate insertion of the locking mechanisms 320, 322, 420, 422 into the openings, as the locking mechanisms 320, 322, 420, 422 can be top-loaded along parallel pathways and do not need to be inserted at an angle relative to the cross connector 300, 400.

The use of parallel openings 308, 310, 408, 410, as well as parallel recesses 304, 306, 404, 406, can be made possible by the configuration of the cavities that receive the shoes 312, 314, 412, 414. As previously discussed with respect to FIGS. 1A-1F, and as shown in FIGS. 7B and 8B, each cavity 316, 318, 416, 418 can extend at a downward angle toward the recesses 304, 306, 404, 406 such that each shoe 312, 314, 412, 414, when moved from within the cavity 316, 318, 416, 418 toward the recess 304, 306, 404, 406, extends in a downward direction. As a result, the shoes 312, 314, 412, 414 will extend at least partially under a spinal fixation element disposed within the recess 304, 306, 404, 406 the thereby engage the spinal fixation element to retain it within the recess 304, 306, 404, 406. This configuration can be present in each of the various cross connectors disclosed herein.

As indicated above, the various cross connectors disclosed herein can also include one or more bend zones formed therein for allowing further angular adjustment of the cross connectors. While the bend zones can be formed at various locations on each cross connector, FIGS. 7A and 8A illustrate a bend zone 330, 430 formed at a substantial mid-portion of the elongate body 302, 403. Each bend zone 330, 430 can be formed using a variety of techniques, but in the illustrated embodiments each bend zone 330, 430 is formed by a decrease in diameter or thickness of the elongate body 302, 402. While the diameter or thickness at the bend zone 330, 430 can vary, the bend zone 330, 430 should allow the elongate body 302, 304 to be deformed and angularly adjusted while still maintaining the structural integrity of the cross connector 300, 400. A person skilled in the art will appreciate that a variety of other techniques can be used to allow for angular adjustment of the cross connectors.

The various shoes used in the various cross connectors disclosed herein can also have a variety of configurations, shapes, and sizes. For example, each shoe can have a cross-sectional shape that is generally cylindrical, oval, or rectangular. FIGS. 9A-11B illustrate shoes 50, 60, 70 having a cylindrical cross-sectional shape, while FIGS. 12A-12C illustrate a shoe 80 having an oval cross-sectional shape. As further shown in FIGS. 8A-12C, each shoe 50, 60, 70, 80 can also have a width $w_1$ at a top portion that is less than a width $w_2$ at a bottom portion, as measured between the external and internal surface 50e, 50i, 60e, 60i, 70e, 70i, 80e, 80i of each shoe 50, 60, 70, 80. In other words, the width of each shoe 50, 60, 70, 80 can decrease from the top to the bottom. This configuration allows only a mid-portion or the bottom portion of each shoe 50, 60, 70, 80 to come into contact with a spinal fixation element disposed within the recess in the elongate body when the shoes 50, 60, 70, 80 are in a locked configuration as a result of the locking mechanism. The distal cone-shaped portion of the locking mechanism, and the front and back surfaces of the shoes can also create a wedge type mechanical advantage such that a force applied to first and second spinal fixation elements by the first and second engagement mechanisms is greater than an axial force applied to the first and second engagement mechanisms by the first and second locking mechanisms. In an exemplary embodiment, such a configuration allows for a ratio of at least about 1.2 (120%), and more preferably about 2.0 (200%) between the axial force applied by the locking mechanism and the force applied to the spinal fixation element by the shoe.

The internal surface 50i, 60i, 70i, 80i of each shoe 50, 60, 70, 80 can also be optimized to facilitate the transfer of force from a locking mechanism that engages and moves the shoe to a spinal fixation rod being engaged by the shoe. For example, FIGS. 9A and 9B illustrate a shoe 50 having a substantially convex internal surface 50i for seating a fastening element. Conversely, FIGS. 10A-10B and 12A-12C illustrate shoes 60, 80 having substantially concave internal surfaces 60i, 80i. As discussed above, however, the shoe of FIGS. 10A-10B has a substantially cylindrical cross-sectional shape while the shoe of FIGS. 12A-12C has a substantially oval cross-sectional shape. As a result, the concave internal surface 60i on the shoe 60 shown in FIGS. 10A-10B has a circular shape, while the concave internal surface 80i on the shoe 80 of FIGS. 12A-12C has an oval shape. FIGS. 11A-11B illustrate another embodiment of a shoe 70 having a planar internal surface 70i. A person skilled in the art will appreciate that the various shoes disclosed herein can have any combination of cross-sectional shapes and surface configurations, as well as a variety of other configurations and features.

Figure 14B:
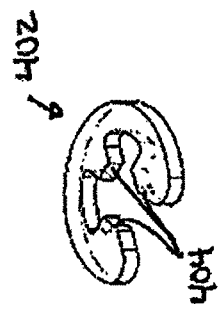
FIG. 14B is a perspective view of the retaining element of FIG. 14A, showing a pin for supporting the deformable members.
Figure 14A:
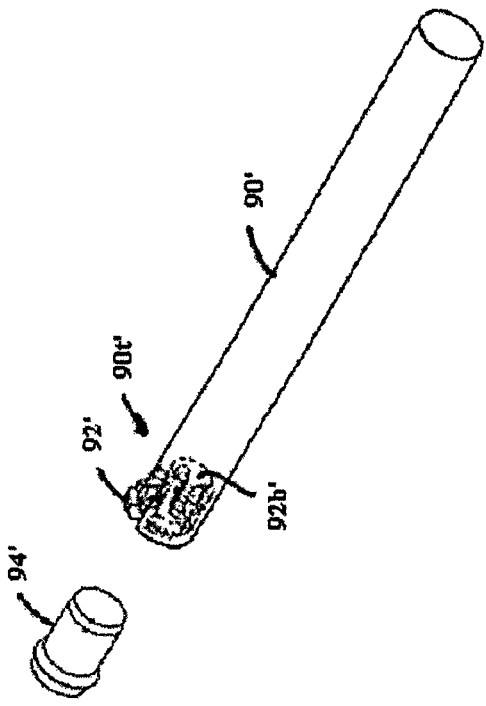
FIG. 14A is a side view of another embodiment of a retaining element having elastically deformable members and an integral flange.
Figure 15B:
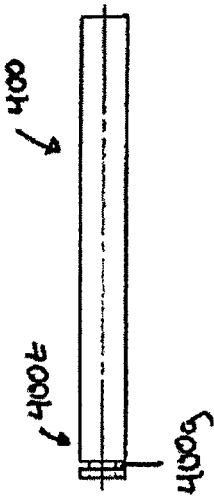
FIG. 15B is a perspective view of a ring member configured to engage the groove formed in the retaining element of FIG. 15A.
Figure 15A:
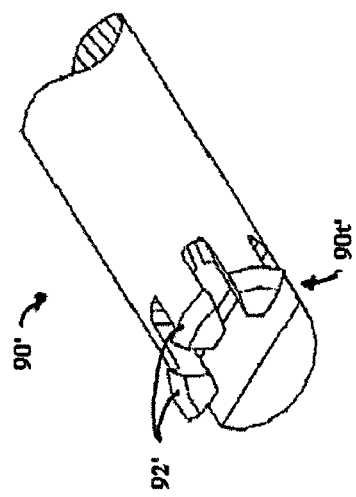
FIG. 15A is a side view of another embodiment of a retaining element having an annular groove formed therein.

As was also previously discussed, the retaining element used to retain the male member within the female member can also have a variety of other configurations. FIGS. 13A-13B illustrate one embodiment of a retaining element that is in the form of deformable tabs 92 formed on the terminal end 90t of a male member 90. As shown, the tabs 92 are formed by creating several cut-outs in the terminal end 90t of the male member 90. Once the male member 90 is inserted through the female member, e.g., during manufacturing, the tabs 92 can be deformed outward such that they extend transverse to an axis $A_{15}$ of the male member 90. As a result, the tabs 92 will prevent the male member 90 from being removed from the female member, as the tabs 92 will have a width that is greater than a width of the first opening formed in the female member. FIGS. 14A-14B illustrate another embodiment of a retaining element that is in the form of deflectable tabs 92' formed on the terminal end 90t' of a male member 90'. During use, the tabs 92' can deflect inward to allow the male member 90 to be inserted through the female member. An insert 94' can then be inserted into a hollowed recess or bore 92b' formed in the terminal end 90t' of the male member 90' to provide support to the tabs 92', i.e., to prevent the tabs 92 from deforming inward. In another embodiment, shown in FIGS. 15A-15B, the terminal end 500t of the male member 500 can optionally include an annular groove 500g formed therein, and a clip 502 can be disposed around and within the annular groove 500g to prevent removal of the male member 500 from the female member. The clip 502 can have a variety of configurations, but FIG. 15B illustrates a c-shaped clip 502 having tabs 504 formed on an inner perimeter thereof for engaging the groove 500g in the male member 500. The clip 502 also preferably has a width that is greater than a width of the first opening in the female member so as to allow the clip 502 to retain the male member 500 within the female member. A person skilled in the art will appreciate that a variety of other retaining mechanisms can be used to retain the male member within the female member.

The present invention also provides various exemplary methods for implanting a cross connector. In one exemplary embodiment, the various cross connectors disclosed herein can be coupled to one or more, and preferably two, spinal fixation elements, such as spinal rods, that are implanted within a patient's spine. Prior to loading the cross connector onto first and second spinal rods, the locking mechanisms are not yet inserted into the openings, or they are only loosely threaded into the openings such that the shoes are in the first retracted position. The shoes can, however, be in the extended position during insertion and the spinal rods can force the shoes into the retracted position. The cross connector is then advanced toward the spinal rods, which can be implanted in the spine such that they generally extend longitudinally along a length of the spinal column. Due to the parallel configuration of the recesses, each cross connector can be simultaneously loaded onto both spinal rods. Depending on the particular configuration, the cross connector can also be adjusted by deforming the bend zone and/or adjusting the male and female members relative to one another. Once the cross connector is properly disposed over the spinal rods, the locking mechanisms can be fully threaded into the openings to contact the internal surface of the shoes to push the shoes toward the recesses, thereby pushing the shoes into contact with the spinal rods. The locking mechanisms are threaded until the shoes lock the rods into the recesses.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal cross connector, comprising:
   an elongate body having opposed first and second ends and opposed top and bottom surfaces;
   first and second recesses formed in the bottom surface adjacent to the first and second ends of the elongate body, the first and second recesses being oriented to enable the elongate body to be simultaneously top-loaded onto first and second spinal fixation elements; and
   first and second bores formed in the top surface of the elongate body and effective to receive first and second locking mechanisms for locking first and second spinal fixation elements within the first and second recesses, the first and second bores having longitudinal axes that are substantially parallel to one another and that are substantially parallel to an axis of loading the elongate body onto first and second spinal fixation elements;
   wherein the first and second recesses comprise substantially concave cavities formed in the bottom surface of the elongate body; and
   wherein each concave cavity has first and second opposed interior sidewalls that are parallel to one another and parallel to the longitudinal axes of the first and second bores in the elongate member.

2. The spinal cross connector of claim 1, further comprising first and second locking mechanisms disposed within the first and second bores and adapted to lock first and second spinal fixation elements within the first and second recesses.

3. The spinal cross connector of claim 2, further comprising first and second engagement elements movably disposed within the elongate body, the first and second locking mechanisms being effective to move the first and second engagement elements to cause the first and second engagement elements to engage and lock first and second spinal fixation elements within the first and second recesses.

4. The spinal cross connector of claim 3, wherein the first and second locking mechanisms and the first and second engagement elements are configured such that a force applied to first and second spinal fixation elements by the first and second engagement elements is greater than an axial force applied to the first and second engagement elements by the first and second locking mechanisms.

5. The spinal cross connector of claim 1, wherein the first and second opposed interior sidewalls of each concave cavity are formed integrally as part of a respective end of the first and second ends of the elongate body.

6. The spinal cross connector of claim 3, wherein the first and second engagement elements are permanently disposed within the elongate body.

7. A spinal cross connector, comprising:
an elongate body having opposed first and second ends and opposed top and bottom surfaces;
first and second concave cavities formed in the bottom surface adjacent to the first and second ends of the elongate body, the first and second concave cavities being oriented to enable the elongate body to be simultaneously top-loaded onto first and second spinal fixation elements;
a first engagement member coupled to the elongate body and configured to move relative to and out of the elongate body into the first concave cavity so as to engage the first spinal fixation element loaded into the first concave cavity;
a second engagement member coupled to the elongate body and configured to move relative to and out of the elongate body into the second concave cavity so as to engage the second spinal fixation element loaded into the second concave cavity;
first and second bores formed in the top surface of the elongate body;
first and second locking mechanisms disposed within the first and second bores, wherein the first and second locking mechanisms are adapted to be retainably disposed within the first and second bores when locking the first and second spinal fixation elements within the first and second concave cavities, and wherein the first and second locking mechanisms are separate, distinct components from the first and second engagement members;
a first snap fit member coupled to the elongate body and configured to snap around the first spinal fixation element loaded into the first concave cavity so as to facilitate retention of the first spinal fixation element therein; and
a second snap fit member coupled to the elongate body and configured to snap around the second spinal fixation element loaded into the second concave cavity so as to facilitate retention of the second spinal fixation element therein.

8. The spinal cross connector of claim 7, wherein the first snap fit member is configured to deflect towards the first end of the elongate member when the first spinal fixation element is loaded into the first concave cavity such that a size of the first concave cavity increases, and the second snap fit member is configured to deflect towards the second end of the elongate member when the second spinal fixation element is loaded into the second concave cavity such that a size of the second concave cavity increases.

9. The spinal cross connector of claim 7, wherein at least one of the first and second snap fit members is configured to provide an audible signal when one of the spinal fixation elements is fully loaded therein.

10. The spinal cross connector of claim 7, wherein at least one of the first and second snap fit members is configured to provide a tactile signal when one of the spinal fixation elements is fully loaded therein.

11. A spinal cross connector, comprising:
an elongate body having opposed first and second ends and opposed top and bottom surfaces;
first and second recesses formed in the bottom surface adjacent to the first and second ends of the elongate body, the first and second recesses being oriented to enable the elongate body to be simultaneously top-loaded onto first and second spinal fixation elements;
a first deflectable member positioned between the first end and the first recess, the first deflectable member being configured to dynamically move away from the first recess in response to the elongate body being top-loaded onto the first spinal fixation element and to dynamically move toward the first recess in response to the first spinal fixation element being fully loaded within the first recess;
a second deflectable member positioned between the second end and the second recess, the second deflectable member being configured to dynamically move away from the second recess in response to the elongate body being top-loaded onto the second spinal fixation element and to dynamically move toward the second recess in response to the second spinal fixation element being fully loaded within the second recess;
first and second bores formed in the top surface of the elongate body and effective to receive first and second locking mechanisms for locking the first and second spinal fixation elements within the first and second recesses;
a first shoe located entirely between the top and bottom surfaces, the first shoe being fixedly disposed within the elongate body and being slidably movable into the first recess while being fixedly disposed within the elongate body; and
a second shoe located entirely between the top and bottom surfaces, the second shoe being fixedly disposed within the elongate body and being slidably movable into the second recess while being fixedly disposed within the elongate body.

12. The spinal cross connector of claim 11, wherein the first shoe is configured to move in response to a force applied by the first locking mechanism received within the first bore to engage and lock the first spinal fixation element within the first recess; and
wherein the second shoe is configured to move in response to a force applied by the second locking mechanism received within the second bore to engage and lock the second spinal fixation element within the second recess.

13. The spinal cross connector of claim 11, wherein the first shoe is slidably movable between a first retracted position in which the first shoe is at least partially disposed within the elongate body and a second extended position in which at least a portion of the first shoe extends into the first recess and engages the first spinal fixation element, and wherein the second shoe is slidably movable between a third refracted position in which the second shoe is at least partially disposed within the elongate body and a fourth extended position in which at least a portion of the second shoe extends into the second recess and engages the second spinal fixation element.

* * * * *